US012582619B2

(12) United States Patent
Kim et al.

(10) Patent No.: US 12,582,619 B2
(45) Date of Patent: Mar. 24, 2026

(54) COMPOUNDS, COMPOSITIONS, AND METHODS FOR TREATING OR AMELIORATING, OR PREVENTING VIRAL INFECTIONS

(71) Applicant: Thomas Jefferson University, Philadelphia, PA (US)

(72) Inventors: Felix Jinhyun Kim, Philadelphia, PA (US); Holly Ramage, Philadelphia, PA (US)

(73) Assignee: Thomas Jefferson University, Philadelphia, PA (US)

( * ) Notice: Subject to any disclaimer, the term of this patent is extended or adjusted under 35 U.S.C. 154(b) by 550 days.

(21) Appl. No.: 17/915,675

(22) PCT Filed: Mar. 30, 2021

(86) PCT No.: PCT/US2021/024914
§ 371 (c)(1),
(2) Date: Sep. 29, 2022

(87) PCT Pub. No.: WO2021/202550
PCT Pub. Date: Oct. 7, 2021

(65) Prior Publication Data

US 2023/0132717 A1 May 4, 2023

Related U.S. Application Data

(60) Provisional application No. 63/001,900, filed on Mar. 30, 2020.

(51) Int. Cl.

| | |
|---|---|
| ***C07D 213/84*** | (2006.01) |
| ***A61K 31/155*** | (2006.01) |
| ***A61K 31/352*** | (2006.01) |
| ***A61P 31/14*** | (2006.01) |
| ***C07C 279/18*** | (2006.01) |
| ***C07D 213/80*** | (2006.01) |
| ***C07D 213/85*** | (2006.01) |
| ***C07D 239/42*** | (2006.01) |

(52) U.S. Cl.
CPC .......... *A61K 31/155* (2013.01); *A61K 31/352* (2013.01); *A61P 31/14* (2018.01); *C07C 279/18* (2013.01); *C07D 213/80* (2013.01); *C07D 213/84* (2013.01); *C07D 213/85* (2013.01); *C07D 239/42* (2013.01)

(58) Field of Classification Search
CPC ..... A61K 31/155; A61K 31/352; A61P 31/14; C07D 213/80; C07D 213/84; C07D 213/85; C07D 239/42; C07C 279/18
USPC .......................................................... 514/256
See application file for complete search history.

(56) References Cited

U.S. PATENT DOCUMENTS

2018/0015153 A1 1/2018 Tang et al.

FOREIGN PATENT DOCUMENTS

| | | |
|---|---|---|
| WO | 2004112687 A2 | 12/2004 |
| WO | 2005095345 A2 | 10/2005 |
| WO | 2014015157 A2 | 1/2014 |
| WO | 2017106312 A1 | 6/2017 |
| WO | 2018112122 A1 | 6/2018 |
| WO | 2018134265 A1 | 7/2018 |

OTHER PUBLICATIONS

"International Search Report and Written Opinion dated Jun. 10, 2021 for International Application No. PCT/US21/24914".
"International Search Report and Written Opinion dated Jun. 9, 2021 for International Appln. No. PCT/US21/24895".
Gordon , et al., "A SARS-CoV-2-Human Protein-Protein Interaction Map Reveals Drug Targets 1-9 and Potential Drug-Repurposing", BioRxiv. Mar. 22, 2020 (Mar. 22, 2020) <https://www.biorxiv.org/content/10.11 O 1 /2020.03.22.002386v1.full>, p. 5, para 1, p. 8, para 1, p. 9, para 2, 1-45.
Kim , et al., "Inhibition of tumor cell growth by Sigma1 ligand mediated translational repression", Biochemical and Biophysical Research Communications 426, 2012, 177-182.
Kim, Felix J., "Introduction to Sigma Proteins: Evolution of the Concept of Sigma Receptors", Handbook of Experimental Pharmacology 244, DOI 10.1007/164_2017_41.
Kim , et al., "σ1 Receptor ligand binding: an open-and-shut case", Nature Structural & Molecular Biology ; vol. 25;, Nov. 2018, 992-995.
Li , et al., "Receptor Recognition Mechanisms of Coronaviruses: a Decade of Structural Studies", Journal of Virology, vol. 89, Nov. 26, 2014, 1954-1964.
Maher , et al., "Small-Molecule Sigma1 Modulator Induces Autophagic Degradation of PD-L1", Molecular Cancer Research; DOI: 10.1158/1541-7786.MCR-17-0166, Nov. 8, 2017.
Oyer , et al., "Small-Molecule Modulators of Sigma1 and Sigma2/TMEM97 in the Context of Cancer: Foundational Concepts and Emerging Themes", Frontiers in Pharmacology, vol. 10; Article 1141, Oct. 2019, 1-16.

(Continued)

*Primary Examiner* — Kristin A Vajda
(74) *Attorney, Agent, or Firm* — Saul Ewing LLP; Domingos J. Silva; Chihao Wang

(57) ABSTRACT

The present disclosure relates, in certain embodiments, to the finding that certain compounds that modulate the activity(ies) of Sigma receptors can be used to disrupt virus life-cycle, infection, and/or dissemination. The compounds contemplated in the disclosure are useful in the prevention, treatment, and/or amelioration of virus infection, either alone or in combination with at least one additional therapeutic agent, which can be an antiviral agent and/or an agent that treats, ameliorates, and/or prevents one or more virus infection symptoms and/or co-morbidities. In certain embodiments, the Sigma receptor is a Sigma-1 receptor (also known as Sigma1) or Sigma-2 receptor (also known as Sigma2 or TMEM97). In certain embodiments, Sigma1 inhibitors/antagonists that cause and/or trigger ER stress and/or autophagy are useful within the methods of the disclosure.

19 Claims, 9 Drawing Sheets

(56) References Cited

OTHER PUBLICATIONS

Salvino , et al., “Novel small molecule guanidine Sigma1 inhibitors for advanced prostate cancer”, Bioorg Med Chem Lett. 27(10), 2017, 2216-2220.
Schrock , et al., “Sequential Cytoprotective Responses to Sigma1 Ligand-Induced Endoplasmic Reticulum Stress”, Mol Pharmacol 84, Nov. 2013, 751-762.
Thomas , et al., “Sigma1 Targeting to Suppress Aberrant Androgen Receptor Signaling in Prostate Cancer”, Cancer Res., vol. 77(9), 2017, 2439-2452.
Ueda , et al., “Antiviral Effect of Guanidine and Its Derivatives Part 1. The Inhibitory Effect of Guanidine on the Multiplication of Poliomyelitis Virus in Tissue Culture”, Keio Journal of Medicine, vol. 10(4), 9 pages, 1961.
Vasallo , et al., “Cellular stress responses in hepatitis C virus infection: Mastering a two-edged sword”, Virus Research, vol. 209, 2015, 100-117.
Vela , “Repurposing Sigma-1 Receptor Ligands for COVID-19 Therapy”, Frontiers in Pharmacology, vol. 11, Article 582310, Nov. 2020.
Zimmer, Carl , “Scientists Identify 69 Drugs to Test Against the Coronavirus”, https://www.nytimes.com/2020/03/22/science/coronavirus-drugs-chi; downloaded, Mar. 25, 2020, 3 pages.
“Extended European Search Report for European Appln. No. 21 77 9330 dated Jun. 24, 2024”.
“Supplementary European Search Report dated Mar. 7, 2024 for European Application No. 21 78 1567”.
Jefferson , et al., “Biaryl guanidine inhibitors of in vitro HCV-IRES activity”, Bioorganic & Medicinal Chemistry Letters, vol. 14, No. 20, 2004, XP029246133, 5139-5143.
Mondotte, et al., “Essential Role of Dengue Virus Envelope Protein N Glycosylation at Asparagine-67 during Viral Propagation.”, Journal of Virology vol. 81, Issue 13, p. 7136-7148 (2007).

COMPOUNDS, COMPOSITIONS, AND METHODS FOR TREATING OR AMELIORATING, OR PREVENTING VIRAL INFECTIONS

CROSS-REFERENCE TO RELATED APPLICATIONS

This application is a 35 U.S.C. § 371 national phase application from, and claims priority to, International Application No. PCT/US2021/024914, filed Mar. 30, 2021, which claims priority under 35 U.S.C. § 119(e) to U.S. Provisional Application No. 63/001,900, filed Mar. 30, 2020, all of which applications are incorporated by reference herein in their entireties.

BACKGROUND

In eukaryotic cells the endoplasmic reticulum (ER) is the primary site of synthesis, folding, and assembly of secreted and integral membrane proteins and their macromolecular complexes. Maintenance of ER protein homeostasis relies on the timely convergence of multiple pathways that detect homeostatic protein concentration thresholds and control the ebb-and-flow of ER proteins. This process is driven by an intricate network of molecular chaperones and transcription factors. Disruption of ER homeostasis activates stress response pathways, including the unfolded protein response (UPR).

The mammalian UPR comprises at least two phases: an initial alarm phase, which is followed by a cytoprotective, adaptive phase in which UPR factors are upregulated to enhance the cellular capacity to process increased concentrations of unfolded protein. Imbalanced or altered capacity to respond to ER stress has been implicated in various diseases and disorders. Protracted ER stress can overwhelm the UPR, leading to autophagy as a secondary survival response. Although the relationship between ER stress, unfolded protein response, and autophagy remains unclear, growing evidence suggests that these responses are likely integrated signaling pathways that modulate cell survival and growth.

Autophagy describes a set of bulk cellular degradation pathways in which large aggregates of misfolded proteins and damaged cellular components, including damaged organelles, are sequestered into membrane bound vesicles called autophagosomes and subsequently targeted for lysosomal degradation. Complete autophagy comprises autophagosome fusion with lysosomes to form autolysosomes, wherein the sequestered proteins and lipids are subsequently degraded by autophagic degradation or flux. Autophagy occurs under basal conditions in many tissues and is involved in cellular differentiation and development. It is also (hyper)activated in conditions of nutrient starvation and cellular stress, to maintain energy levels and to sequester and remove damaged and cytotoxic cellular components. Thus, autophagy plays important roles in cellular homeostasis and disease prevention, and defective autophagy has been implicated in neurodegenerative disease and cancer.

Sigma receptors are distinct from classical opioid receptors. Sigma1 is highly conserved among mammals (greater than 80% amino acid identity), but shares no significant homology with any traditional receptor family or other mammalian protein. Cloned Sigma1 is a 26 kilodalton integral membrane protein found primarily in the ER, and can translocate to the plasma membrane, other organelles, and endoplasmic membrane microdomains. Recent work has described Sigma ligand-induced cell death by lysosomal destabilization and oxidative stress.

There is a need in the art to identify compounds useful in the treatment of viral infections, such as but not limited to coronavirus infections, such as but not limited to SARS-CoV and/or SARS-CoV-2. The present disclosure addresses this unmet need.

BRIEF SUMMARY

The invention provides a compound of formula (I):

(I)

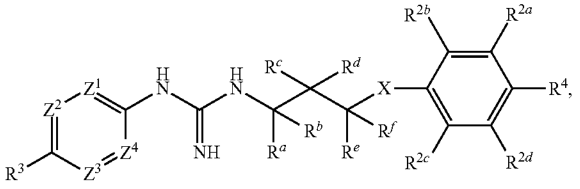

wherein:

one of the following applies: (a) $Z^1$ is $CR^{1a}$; $Z^2$ is N; $Z^3$ is $CR^{1c}$ or N; $Z^4$ is $CR^{1d}$; (b) $Z^1$ is N; $Z^2$ is $CR^{1b}$; $Z^3$ is $CR^{1c}$; $Z^4$ is $CR^{1d}$ or N; (c) $Z^1$ is $CR^{1a}$; $Z^2$ is N; $Z^3$ is $CR^{1c}$; $Z^4$ is N; (d) $Z^1$ is N; $Z^2$ is $CR^{1b}$; $Z^3$ is N; $Z^4$ is $CR^{1d}$;

X is selected from the group consisting of bond and O;

each occurrence of $R^{1a}$, $R^{1b}$, $R^{1c}$, and $R^{1d}$ is independently selected from the group consisting of $C_1$-$C_6$ alkyl, $C_1$-$C_6$ fluoroalkyl, $C_1$-$C_6$ heteroalkyl, F, Cl, Br, I, —CN, —$NO_2$, —$OR^5$, —$SR^5$, —S(=O)$R^5$, —S(=O)$_2$ $R^5$, —NHS(=O)$_2R^5$, —C(=O)$R^5$, —OC(=O)$R^5$, —$CO_2R^5$, —$CO_2R^5$, —CH$(R^5)_2$, —N$(R^5)_2$, —C(=O)N$(R^5)_2$, —OC(=O)N$(R^5)_2$, —NHC(=O)NH$(R^5)$, —NHC(=O)$R^5$, —NHC(=O)O$R^5$, —C(OH)$(R^5)_2$, and —C$(NH_2)(R^5)_2$;

each occurrence of $R^{2a}$, $R^{2b}$, $R^{2c}$, and $R^{2d}$ is independently selected from the group consisting of $C_1$-$C_6$ alkyl, $C_1$-$C_6$ fluoroalkyl, $C_1$-$C_6$ heteroalkyl, F, Cl, Br, I, —CN, —$NO_2$, —$OR^5$, —$SR^5$, —S(=O)$R^5$, —S(=O)$_2$ $R^5$, —NHS(=O)$_2R^5$, —C(=O)$R^5$, —OC(=O)$R^5$, —$CO_2R^5$, —$CO_2R^5$, —CH$(R^5)_2$, —N$(R^5)_2$, —C(=O)N$(R^5)_2$, —OC(=O)N$(R^5)_2$, —NHC(=O)NH$(R^5)$, —NHC(=O)$R^5$, —NHC(=O)O$R^5$, —C(OH)$(R^5)_2$, and —C$(NH_2)(R^5)_2$;

$R^3$ is selected from the group consisting of CN, F, Cl, Br, I, $C_1$-$C_6$ haloalkyl, $C_1$-$C_6$ haloalkoxy, and —C(O)O$R^6$;

$R^4$ is selected from the group consisting of CN, F, Cl, Br, I, $C_1$-$C_6$ haloalkyl, $C_1$-$C_6$ haloalkoxy, and —C(O)O$R^7$;

each occurrence of $R^5$ is independently selected from the group consisting of H, $C_1$-$C_6$ alkyl, $C_1$-$C_6$ heteroalkyl, aryl, and —$C_1$-$C_3$ alkyl-($C_3$-$C_6$ cycloalkyl), wherein the alkyl, heteroalkyl, aryl, or cycloalkyl group is optionally substituted;

$R^6$ is selected from the group consisting of H, $C_1$-$C_6$ alkyl, $C_1$-$C_6$ heteroalkyl, and $C_3$-$C_6$ cycloalkyl, wherein the alkyl, heteroalkyl, or cycloalkyl group is optionally substituted;

$R^7$ is selected from the group consisting of H, $C_1$-$C_6$ alkyl, $C_1$-$C_6$ heteroalkyl, and $C_3$-$C_6$ cycloalkyl, wherein the alkyl, heteroalkyl, or cycloalkyl group is optionally substituted; and each occurrence of $R^a$, $R^b$, $R^c$, $R^d$, $R^e$, and $R^f$ is independently selected from the group consisting of H and $CH_3$, with the proviso that, if Y is $CR^{1c}$ and Z is $CR^{1d}$, then at least one of $R^a$, $R^b$, $R^c$, $R^d$, $R^e$, and $R^f$ is $CH_3$. or a salt, solvate, enantiomer, diastereoisomer, tautomer, or N-oxide thereof.

In certain embodiments, each occurrence of $R^{1a}$, $R^{1b}$, $R^{1c}$, and $R^{1d}$ is independently selected from the group consisting of $C_1$-$C_6$ alkyl, $C_1$-$C_6$ fluoroalkyl, $C_1$-$C_6$ heteroalkyl, F, Cl, Br, I, —CN, —$NO_2$, and —$OR^5$.

In certain embodiments, each occurrence of $R^{2a}$, $R^{2b}$, $R^{2c}$, and $R^{2d}$ is independently selected from the group consisting of $C_1$-$C_6$ alkyl, $C_1$-$C_6$ fluoroalkyl, $C_1$-$C_6$ heteroalkyl, F, Cl, Br, I, —CN, —$NO_2$, and —$OR^5$.

In certain embodiments, $R^3$ is CN, F, Cl, Br, I, —$CF_3$, —$CHF_2$, —$OCF_3$, —$OCHF_2$, —C(O)OH, or —C(O)OMe.

In certain embodiments, $R^4$ is CN, F, Cl, Br, I, —$CF_3$, —$CHF_2$, —$OCF_3$, —$OCHF_2$, —C(O)OH, or —C(O)OMe.

In certain embodiments, the compound is selected from the group consisting of: 1-(6-cyano-5-methoxypyridin-3-yl)-3-(3-methyl-3-(4-(trifluoromethyl)phenoxy)butyl)guanidine; 1-(6-cyano-5-methoxypyridin-3-yl)-3-(2,2-dimethyl-3-(4-(trifluoromethyl)phenoxy)propyl)guanidine; 1-(5-cyano-4-methoxypyridin-2-yl)-3-(3-methyl-3-(4-(trifluoromethyl)phenoxy)butyl)guanidine; 1-(3,4-dichlorophenyl)-3-(3-methyl-3-(4-(trifluoromethyl)phenoxy)butyl)guanidine; 1-(6-chloro-5-fluoropyridin-3-yl)-3-(3-methyl-3-(4-(trifluoromethyl)phenoxy)butyl)guanidine; 1-(5-cyano-4-methoxypyridin-2-yl)-3-(3-methyl-3-(4-(trifluoromethyl)phenyl)butyl)guanidine; methyl 6-(3-(3-methyl-3-(4-(trifluoromethyl)phenyl)butyl)guanidino)nicotinate; methyl 6-(3-(2,2-dimethyl-3-(4-(trifluoromethyl)phenoxy)propyl)guanidino)nicotinate; 1-(3-methyl-3-(4-(trifluoromethyl)phenoxy)butyl)-3-(2-(trifluoromethyl)pyrimidin-5-yl)guanidine; 1-(6-cyano-5-methoxypyridin-3-yl)-3-(3-methyl-3-(4-(trifluoromethyl)phenoxy)butyl)guanidine; or a salt, solvate, tautomer, or N-oxide thereof.

The invention provides a pharmaceutical composition comprising at least one pharmaceutically acceptable carrier and at least one compound of the disclosure.

In certain embodiments, the pharmaceutical composition further comprises at least one additional antiviral agent and/or at least one agent that treats, ameliorates, and/or prevents one or more virus infection symptoms and/or co-morbidities.

In certain embodiments, the pharmaceutical composition is formulated for administration by at least one of oral, nasal, rectal, intravaginal, parenteral, buccal, sublingual, and/or topical routes.

The invention provides a method of disrupting virus lifecycle, infection, and/or dissemination in a virus-infected subject, and/or preventing and/or minimizing virus infection and/or dissemination in a subject.

The invention provides a method of inhibiting, minimizing, and/or preventing formation of virus particles in a virus-infected subject.

The invention provides a method of altering production, post-translational modification, assembly, maturation, and/or functional cell surface expression of at least one virus protein involved in viral entry and/or viral infection in a subject's cell.

The invention provides a method of initiating and/or stimulating selective autophagosomal, lysosomal, and/or proteasomal degradation of at least one virus protein involved in viral entry and/or viral infection in a subject's cell.

The invention provides a method of decreasing and/or inhibiting increase of amount, concentration, and/or production of at least one virus protein involved in viral entry and/or viral infection in a subject's cell.

The invention provides a method of altering and/or disturbing subcellular localization and/or virus promoting activity of at least one virus protein involved in viral entry and/or viral infection in a subject's cell.

The invention provides a method of minimizing and/or preventing incorporation of a surface viral protein into a virion in a virus-infected eukaryotic cell.

In certain embodiments, the method comprises administering to the subject a therapeutically effective amount of a Sigma1 inhibitor/antagonist that causes and/or triggers ER stress and/or autophagy in the subject.

In certain embodiments, the method comprises administering to the subject a therapeutically effective amount of a compound of Formula (I), as described elsewhere herein, or a salt, solvate, or N-oxide thereof and any combinations thereof.

In certain embodiments, the virus comprises a flavivirus.

In certain embodiments, the flavivirus comprises at least one of at least one of Apoi virus, Aroa virus, Bamaga virus, Bagaza virus, Banzi virus, Bouboui virus, Bukalasa bat virus, Cacipacore virus, Carey Island virus, Cowbone Ridge virus, Dakar bat virus, Dengue virus, Edge Hill virus, Entebbe bat virus, Gadgets Gully virus, Ilheus virus, Israel turkey meningoencephalomyelitis virus, Japanese encephalitis virus, Jugra virus, Jutiapa virus, Kadam virus, Kedougou virus, Kokobera virus, Koutango virus, Kyasanur Forest disease virus, Langat virus, Louping ill virus, Meaban virus, Modoc virus, Montana myotis leukoencephalitis virus, Murray Valley encephalitis virus, Ntaya virus, Omsk hemorrhagic fever virus, Phnom Penh bat virus, Powassan virus, Rio Bravo virus, Royal Farm virus, Saboya virus, Saint Louis encephalitis virus, Sal Viej a virus, San Perlita virus, Saumarez Reef virus, Sepik virus, Tembusu virus, Tick-borne encephalitis virus, Tyuleniy virus, Uganda S virus, Usutu virus, Wesselsbron virus, West Nile virus, Yaounde virus, Yellow fever virus, Yokose virus, and Zika virus.

In certain embodiments, the virus comprises a Coronavirus.

In certain embodiments, the Coronavirus comprises at least one of an Alphacoronavirus, a Betacoronavirus, a Gammacoronavirus, and a Deltacoronavirus.

In certain embodiments, the Coronavirus comprises at least one of MERS-CoV, SARS-CoV, and SARS-CoV-2.

In certain embodiments, the virus is a Coronavirus and wherein the at least one coronavirus protein comprises NSP6 and/or a S glycoprotein.

In certain embodiments, the compound is administered to the subject as a pharmaceutical composition further comprising a pharmaceutically acceptable carrier.

In certain embodiments, the subject is further administered at least one additional antiviral agent and/or at least one agent that treats, ameliorates, and/or prevents one or more virus infection symptoms and/or co-morbidities.

In certain embodiments, the compound is administered to the subject by a route comprising oral, nasal, rectal, intravaginal, parenteral, buccal, sublingual, or topical.

In certain embodiments, the subject is a mammal.

In certain embodiments, the mammal is a human.

BRIEF DESCRIPTION OF THE DRAWINGS

The following detailed description of specific embodiments of the disclosure will be better understood when read in conjunction with the appended drawings. For the purpose of illustrating the disclosure, exemplary embodiments are shown in the drawings. It should be understood, however, that the disclosure is not limited to the precise arrangements and instrumentalities of the embodiments shown in the drawings.

FIG. 1A: TMPRSS2 transcript levels decrease in Sigma1 siRNA (siR) mediated knockdown LNCaP cells. FIG. 1B: TMPRSS2 transcript decreased in LNCaP cells treated with Sigma1 modulator IPAG (also known as 1-(4-iodophenyl)-3-(2-adamantyl)guanidine; 10 μM). FIGS. 1C-1D: AR luciferase reporter assay shows inhibition of dihydrotesterone (DHT) induced AR transcriptional activity by IPAG (FIG. 1C), CT189 (also known as 1-(4-chlorophenyl)-3-(3-(4-fluorophenoxy)-prop-1-yl)guanidine; FIG. 1D).

FIG. 2A: Sigma1 protein expression in lung tissue. IHC performed with anti-Sigma1 antibody (described in Schrock et al, 2013, Mol Pharmacol 84:751-762; and Thomas et al, 2017, Cancer Research, DOI: 10.1158/0008-5472.CAN-16-1055). Inset of indicated area shown below. FIG. 2B: SIGMAR1 transcript levels in subpopulations of lung cells: Alveolar type I (AT1) and type II (AT2) epithelial cells, Ciliated cells, club cells, epithelial cells, fibroblasts, immune (monocytes, T-cells) and lymphatic endothelial (Lymph.Endo.) cells. Analysis was performed using dataset published in Lukassen et al, 2020, The EMBO J. e105114). CPM summed across each cell type per patient. FIG. 2C: Pearson correlation of SIGMAR1 and TMPRSS2 and ACE2 mRNA in lung AT2 cells. FIG. 2D: Pearson correlation of ACE2 and TMPRSS2 in lung AT2 cells.

DETAILED DESCRIPTION

Figure 1A:
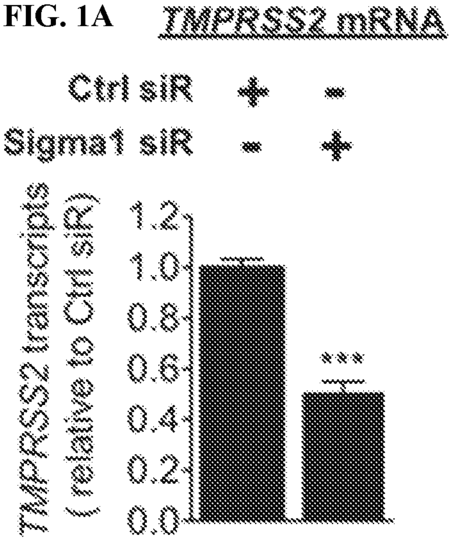
FIGS. 1A-1D illustrate the finding that Sigma1 modulators suppress TMPRSS2 mRNA transcript levels in part by allosteric inhibition of androgen receptor (AR).
Figure 1B:
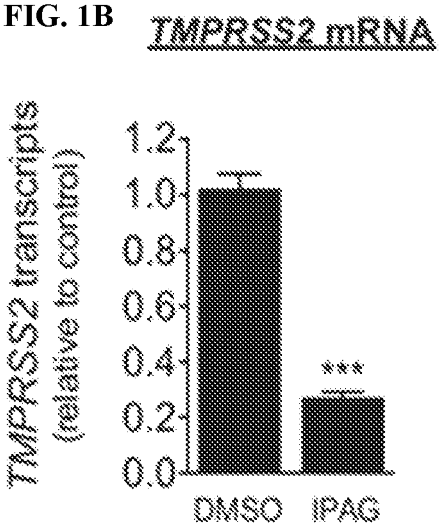
Figure 1C:
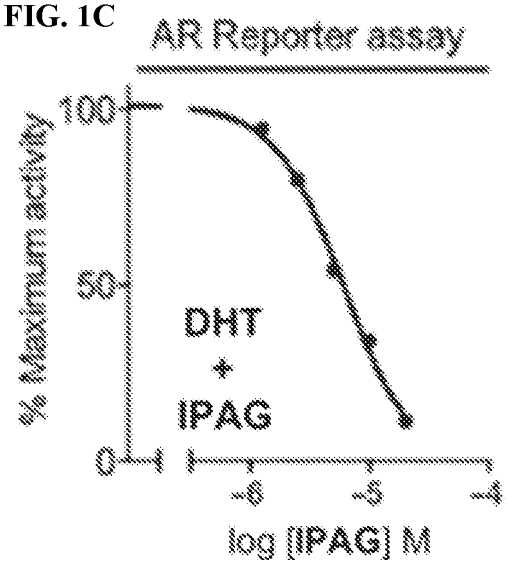
Figure 1D:
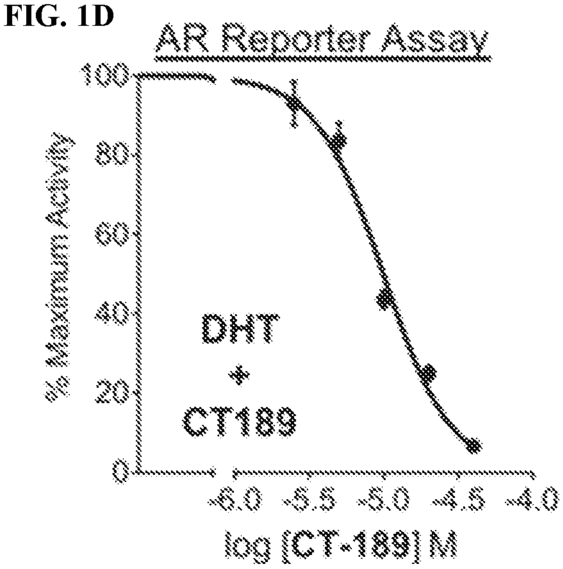

The present disclosure relates to the finding that certain compounds that bind to and inhibit activity of the Sigma receptor modulators can be used to disrupt viral lifecycle, infection, and/or dissemination. The compounds contemplated in the disclosure are useful in the treatment or amelioration of viral infection, either alone or in combination with at least one additional therapeutic agent, which can be an antiviral agent and/or an agent that treats, ameliorates, and/or ameliorates one or more viral infection symptoms and/or co-morbidities.

In other embodiments, the Sigma receptor is a Sigma1 receptor (also known as Sigma1). In certain embodiments, the virus comprises a flavivirus. In other embodiments, the flavivirus comprises at least one of Zika virus, Dengue virus, and Powassan virus. In yet other embodiments, the flavivirus comprises at least one of Apoi virus, Aroa virus, Bamaga virus, Bagaza virus, Banzi virus, Bouboui virus, Bukalasa bat virus, Cacipacore virus, Carey Island virus, Cowbone Ridge virus, Dakar bat virus, Dengue virus, Edge Hill virus, Entebbe bat virus, Gadgets Gully virus, Ilheus virus, Israel turkey meningoencephalomyelitis virus, Japanese encephalitis virus, Jugra virus, Jutiapa virus, Kadam virus, Kedougou virus, Kokobera virus, Koutango virus, Kyasanur Forest disease virus, Langat virus, Louping ill virus, Meaban virus, Modoc virus, Montana myotis leukoencephalitis virus, Murray Valley encephalitis virus, Ntaya virus, Omsk hemorrhagic fever virus, Phnom Penh bat virus, Powassan virus, Rio Bravo virus, Royal Farm virus, Saboya virus, Saint Louis encephalitis virus, Sal Vieja virus, San Perlita virus, Saumarez Reef virus, Sepik virus, Tembusu virus, Tick-borne encephalitis virus, Tyuleniy virus, Uganda S virus, Usutu virus, Wesselsbron virus, West Nile virus, Yaounde virus, Yellow fever virus, Yokose virus, and Zika virus.

In certain embodiments, the virus comprises a Coronavirus. In other embodiments, the Coronavirus comprises at least one of an Alphacoronavirus, a Betacoronavirus, a Gammacoronavirus, and a Deltacoronavirus. In yet other embodiments, the Coronavirus comprises at least one of MERS-CoV, SARS-CoV, and SARS-CoV-2, and any variants thereof.

Sigma1 (gene name SIGMAR1; also known as sigma1-receptor) is a unique pharmacologically-responsive intracellular integral membrane scaffolding protein. Sigma1 is enriched in the secretory pathway, particularly the endoplasmic reticulum (ER) of most cells. Sigma1 itself has no known intrinsic signaling or enzymatic activity, rather it allosterically modulates the intracellular signaling and activities of its associated proteins. Sigma1 physically associates with multiple integral membrane proteins and functions via protein-protein interactions to regulate their stability, transport, and degradation in a pharmacologically controllable manner. The multifunctionality of Sigma1 enables it to regulate lipid and protein homeostasis at multiple levels and it plays a critical role in protein synthesis, processing, trafficking, assembly, and quality control in the secretory pathway of cells. Thus, targeting Sigma1 enables selective modulation of multiple cellular processes via one drug target. Certain Sigma1 modulators can block glycosylation, maturation, and transport of integral membrane glycoproteins in the ER, block their cell surface expression, and trigger lysosomal degradation. In certain embodiments, these features of Sigma1 modulators can be exploited to suppress viral proteins in infected cells and/or suppress viral replication and/or suppress production of viral particles. In certain embodiments, certain Sigma1 modulators can be used to minimize and/or reduce viral load and/or block viral dissemination.

The on-target actions of Sigma1 modulators do not induce adverse effects. Additionally, SIGMAR1 knockout (KO) mice are viable and do not display a phenotype overtly different from wild type mice, indicating that Sigma1 inhibition has minimal impact on normal tissues.

In certain embodiments, Sigma1 inhibitors/antagonists that trigger ER stress and/or autophagy are useful within the methods of the disclosure. In certain embodiments, certain Sigma1 inhibitors/antagonists can suppress viral infection, replication, and subsequent cytopathic effects (CPE). In certain embodiments, certain Sigma1 inhibitors/antagonists can suppress SARS-CoV-2 infection, replication, and subsequent cytopathic effects (CPE). In certain embodiments, certain Sigma1 inhibitors/antagonists can suppress S protein maturation and trigger its degradation via ER stress associated proteasomal or lysosomal mechanisms, thus preventing S protein incorporation into SARS-CoV-2 virions and/or suppressing TMPRSS2 protein levels and cell surface localization on susceptible host cells. In certain embodiments, certain Sigma1 inhibitors/antagonists can suppress maturation of at least one surface viral protein and trigger its degradation via ER stress associated proteasomal or lysosomal mechanisms, thus preventing incorporation of the at least one surface protein into the virion. In certain embodiments, certain Sigma1 inhibitors/antagonists induce degradation of a surface viral protein which is key for viral infection, and this results in reduced or weakened viral infection and/or reduced viral loads. In certain embodiments, Sigma1 inhibitor/antagonist-induced degradation of SARS-CoV-2 S protein and suppression of TMPRSS2 expression can restrict SARS-CoV-2 infection, reduced viral loads, and/or reduced pathology in the lungs of animals treated with certain Sigma1 inhibitors/antagonists.

In one aspect, any embodiment described herein is not limited to SARS-CoV-2, and is also applicable to other viruses that use a similar route of entry and mechanism of replication as SARS-Cov-2, such as viruses that utilize at least one surface viral protein as a means to penetrate a host cell.

As described herein, Sigma1 and Sigma2 targeting therapies can be used to treat infection by severe acute respiratory syndrome coronavirus (SARS-CoV and/or SARS-CoV-2) and related infectious agents. In certain embodiments, the compounds contemplated in the disclosure can be used to treat or ameliorate infection caused by SARS-CoV and/or SARS-CoV-2 and related infection agents without promoting undesirable and/or treatment-limiting central nervous system (CNS)-related side effects.

In certain embodiments, the compounds contemplated in the disclosure trigger pathways that regulate protein and lipid homeostasis in the secretory pathway (endoplasmic reticulum, Golgi, plasma membrane, and associated vesicles including lysosomes, autolysosomes, and endolysosomes). The compounds contemplated in the disclosure, but not all compounds with affinity for Sigma, can be used to selectively regulate protein trafficking, production, and degradation. These compounds contemplated in the disclosure do so in part by triggering the unfolded protein response (UPR) and selective autophagy. Such biological modulations are useful in treating or ameliorating infection caused by SARS-CoV, SARS-Cov-2, and related infectious agents.

In certain embodiments, Sigma1 physically interacts with the SARS-CoV-2 protein Non-Structural protein 6 (NSP6), which is a membrane-spanning integral component of the SARS-CoV-2 viral replication complex that is implicated in double membrane vesicle (DMV) formation. In certain embodiments, SARS-CoV-2 protein NSP6 plays a role in regulation of autophagy of the infected cell. However, at the time of the present disclosure there was no knowledge whether compounds with affinity for Sigma1 and Sigma2 would have any activity in the SARS-CoV-2 disease model: it was unclear which Sigma targeted compounds would be efficacious in treating SARS-CoV-2 and which would bind to Sigma1 and/or Sigma2 and demonstrate actual efficacy in the disease model. In certain embodiments, a compound useful within the present methods triggers UPR, autophagy, and lysosomal mechanisms via Sigma receptors, and yet has limited and/or manageable side effects, which do not limit their utility as therapeutic agents. In certain embodiments, the compounds contemplated within the disclosure induce the UPR, autophagy, and lysosomal mechanisms as described elsewhere herein, but with improved safety and efficacy.

In certain embodiments, the compounds contemplated within the disclosure promote autophagic degradation of NSP6 in a coronavirus-infected cell. In certain embodiments, the compounds contemplated within the disclosure decrease or inhibit increase of NSP6 concentration in a coronavirus-infected cell and/or alter the subcellular localization and/or virus promoting activity of NSP6. In certain embodiments, the compounds contemplated within the disclosure inhibit, minimize, or prevent formation of new coronavirus particles in a coronavirus-infected cell. In certain embodiments, the compounds contemplated within the disclosure alter production, post-translational modification, assembly, and functional cell surface expression of proteins involved in host cell viral entry and/or host cell infection such as but not limited to NSP6 and/or a coronavirus spike (S) glycoprotein. In certain embodiments, the compounds contemplated within the disclosure trigger the selective autophagosomal, lysosomal, and proteasomal degradation of coronavirus proteins including NSP6 and/or a spike (S) glycoprotein in the host cell. In certain embodiments, the compounds contemplated within the disclosure suppress protein production (such as but not limited to NSP6 and/or a S glycoprotein) in the host cell.

In certain embodiments, activities of compounds contemplated within the disclosure can be assessed using one or more of the following assays: (1) viral infectivity measured by plaque assay; (2) viral replication and production assay by virus isolation and protein and nucleotide analysis (methods similar to current RT-PCR based detection methods); (3) cell based assay measuring NSP6 levels and/or localization; (4) cell based and biochemical assays measuring induction (formation of autophagosomes) and completion of autophagy (autophagic flux/degradation of cargo) mediated by NSP6; (5) cell-to-cell fusion assay with recombinant S protein expressing cells; (6) syncytium assay with recombinant S protein expressing cells; (7) NSP6 and S glycoprotein levels by immunoblot and/or fluorescent and/or luciferase tagged recombinant versions of these proteins; (8) protein localization by subcellular fractionation and immunoblot, confocal imaging of fluorescence tagged protein or untagged proteins by immunocytochemistry/fluorescence microscopy; (9) pseudovirus infection assay with SARS-CoV-2 S pseudovirions to measure virus entry; (10) correlation of results from (1)-(9) to "connect the dots" to determine which Sigma modulator impacted activities correlate with decreased infectivity.

Coronaviruses are entirely dependent on the host's cellular machinery to replicate. In certain embodiments, Sigma1 targeted agents can be used to prevent SARS-CoV-2 from co-opting the host cell's machinery to replicate and produce new infectious viral particles. In certain embodiments, Sigma1 modulators can disrupt two proteins crucial to infection and replication: Spike (S) protein (targeting the virus) and TMPRSS2 (modifying the host cell). S protein is a SARS-CoV-2 integral membrane glycoprotein that enables SARS-CoV-2 to recognize and infect host cells. TMPRSS2 is a cellular membrane glycoprotein that acts as a cofactor to angiotensin converting enzyme 2 (ACE2), the cellular receptor recognized by S protein. TMPRSS2 enhances infection by cleaving and thus activating the S protein to trigger membrane fusion that enables viral entry into host cells. Elevated TMPRSS2 on host cells dramatically increases susceptibility to SARS-CoV-2 infection.

The present disclosure includes any compound contemplated within the disclosure, as well as compositions comprising the same, wherein the compositions optionally further comprise at least one additional therapeutic agent and/or at least one pharmaceutically acceptable carrier.

In certain embodiments, the compounds contemplated within the disclosure have improved drug-like properties over compounds known in the art to bind to and modulate the Sigma receptor. In other embodiments, the compounds contemplated within the disclosure do not cross the blood-brain barrier. In yet other embodiments, the compounds contemplated within the disclosure cross the blood-brain barrier.

The compounds contemplated within the disclosure can be characterized by pharmacological, cellular, biochemical, in vivo, pharmacokinetics, or pharmacodynamics properties. Selected examples of characterization studies include, but are not limited to, Sigma1-ligand binding properties, signaling pathway analysis and/or characterization, proteomic analysis of Sigma1 protein associations in response to Sigma ligand treatment, tumor, brain response, and toxicity.

The entire disclosures of WO2014/015157 and US2015/0166472 are incorporated herein in their entireties by reference.

Definitions

Unless defined otherwise, all technical and scientific terms used herein have the same meaning as commonly understood by one of ordinary skill in the art to which this disclosure belongs. Although any methods and materials similar or equivalent to those described herein can be used in the practice or testing of the present disclosure, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

The term "abnormal," when used in the context of organisms, tissues, cells or components thereof, refers to those organisms, tissues, cells or components thereof that differ in at least one observable or detectable characteristic (e.g., age, treatment, time of day, etc.) from those organisms, tissues, cells or components thereof that display the "normal" (expected) respective characteristic. Characteristics that are normal or expected for one cell or tissue type might be abnormal for a different cell or tissue type.

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

A disease or disorder is "alleviated" or "ameliorated" if the severity of a symptom of the disease or disorder, the frequency with which such a symptom is experienced by a patient, or both, is reduced.

As used herein, the term "Sigma" refers to the Sigma1 receptor (Sigma1), Sigma2 receptor (Sigma2), any splice variant thereof or any isoform thereof.

As used herein, a "Sigma receptor modulator" is a compound that binds to the Sigma receptor and modifies the activity or biological function of the receptor as compared to the activity or biological function of the receptor in the absence of the modulator. In certain embodiments, the modulator can activate the receptor and thus cause a biological response that is enhanced over the baseline activity of the unbound receptor. In certain embodiments, the modulator cannot activate the receptor thoroughly and thus causes a biological response that is smaller in magnitude compared to those of full modulators. In certain embodiments, the modulator can bind to the receptor but does not activate it, resulting in receptor blockage and inhibiting the binding of other modulators. Such an modulator does not diminish the baseline intracellular response in the absence of an modulator. In certain embodiments, the modulator can function as a putative antagonist, agonist, or as an inverse agonist, which reduces the activity of the receptor by inhibiting its constitutive activity.

The terms "patient," "subject," "individual," and the like are used interchangeably herein, and refer to any animal, or cells thereof whether in vitro or in situ, amenable to the methods described herein. In a non-limiting embodiment, the patient, subject or individual is a human.

A "therapeutic" treatment is a treatment administered to a subject who exhibits signs of pathology, for the purpose of diminishing or eliminating those signs.

As used herein, the term "treatment" or "treating" is defined as the application or administration of a therapeutic agent, i.e., a compound of the disclosure (alone or in combination with another pharmaceutical agent), to a patient, or application or administration of a therapeutic agent to an isolated tissue or cell line from a patient (e.g., for diagnosis or ex vivo applications), who has a condition contemplated herein and/or a symptom of a condition contemplated herein, with the purpose to cure, heal, alleviate, relieve, alter, remedy, ameliorate, improve or affect a condition contemplated herein and/or the symptoms of a condition contemplated herein. Such treatments may be specifically tailored or modified, based on knowledge obtained from the field of pharmacogenomics.

As used herein, the term "composition" or "pharmaceutical composition" refers to a mixture of at least one compound useful within the disclosure with a pharmaceutically acceptable carrier. The pharmaceutical composition facilitates administration of the compound to a patient or subject. Multiple techniques of administering a compound exist in the art including, but not limited to, intravenous, oral, aerosol, parenteral, ophthalmic, pulmonary and topical administration.

The phrase "therapeutically effective amount," as used herein, refers to an amount that is sufficient or effective to prevent or treat (delay or prevent the onset of, prevent the progression of, inhibit, decrease or reverse) a disease or condition associated with the Sigma receptor, including alleviating symptoms of such diseases.

As used herein, the terms "effective amount," "pharmaceutically effective amount" and "therapeutically effective amount" refer to a nontoxic but sufficient amount of an agent to provide the desired biological result. That result may be reduction and/or alleviation of the signs, symptoms, or causes of a disease, or any other desired alteration of a biological system. An appropriate therapeutic amount in any individual case may be determined by one of ordinary skill in the art using routine experimentation.

An "effective amount" of a delivery vehicle is that amount sufficient to effectively bind or deliver a compound.

As used herein, the term "potency" refers to the dose needed to produce half the maximal response ($ED_{50}$).

As used herein, the term "efficacy" refers to the maximal effect ($E_{max}$) achieved within an assay.

As used herein, the term "pharmaceutically acceptable" refers to a material, such as a carrier or diluent, which does not abrogate the biological activity or properties of the compound, and is relatively non-toxic, i.e., the material may be administered to an individual without causing undesirable biological effects or interacting in a deleterious manner with any of the components of the composition in which it is contained.

As used herein, the language "pharmaceutically acceptable salt" refers to a salt of the administered compounds prepared from pharmaceutically acceptable non-toxic acids, including inorganic acids, organic acids, solvates, hydrates, or clathrates thereof. Examples of such inorganic acids are hydrochloric, hydrobromic, hydroiodic, nitric, sulfuric, phosphoric, acetic, hexafluorophosphoric, citric, gluconic, benzoic, propionic, butyric, sulfosalicylic, maleic, lauric, malic, fumaric, succinic, tartaric, amsonic, pamoic, p-tolunenesulfonic, and mesylic. Appropriate organic acids may be selected, for example, from aliphatic, aromatic, carboxylic and sulfonic classes of organic acids, examples of which are formic, acetic, propionic, succinic, camphorsulfonic, citric, fumaric, gluconic, isethionic, lactic, malic, mucic, tartaric, para-toluenesulfonic, glycolic, glucuronic, maleic, furoic, glutamic, benzoic, anthranilic, salicylic, phenylacetic, mandelic, embonic (pamoic), methanesulfonic, ethanesulfonic, pantothenic, benzenesulfonic (besylate), stearic, sulfanilic, alginic, galacturonic, and the like. Furthermore, pharmaceutically acceptable salts include, by way of non-limiting example, alkaline earth metal salts (e.g., calcium or magnesium), alkali metal salts (e.g., sodium-dependent or potassium), and ammonium salts.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the disclosure within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the disclosure, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful within the disclosure, and are physiologically acceptable to the patient. Supplementary active compounds may also be incorporated into the compositions. The "pharmaceutically acceptable carrier" may further include a pharmaceutically acceptable salt of the compound useful within the disclosure. Other additional ingredients that may be included in the pharmaceutical compositions used in the practice of the disclosure are known in the art and described, for example in Remington's Pharmaceutical Sciences (Genaro, Ed., Mack Publishing Co., 1985, Easton, PA), which is incorporated herein by reference.

As used herein, the term "alkyl," by itself or as part of another substituent means, unless otherwise stated, a straight or branched chain hydrocarbon having the number of carbon atoms designated (i.e. $C_{1-6}$ means one to six carbon atoms) and including straight, branched chain, or cyclic substituent groups. Examples include methyl, ethyl, propyl, isopropyl, butyl, isobutyl, tert-butyl, pentyl, neopentyl, hexyl, and cyclopropylmethyl. Most preferred is $(C_1\text{-}C_6)$alkyl, particularly ethyl, methyl, isopropyl, isobutyl, n-pentyl, n-hexyl and cyclopropylmethyl.

As used herein, the term "substituted alkyl" means alkyl as defined above, substituted by one, two or three substituents selected from the group consisting of halogen, —OH, alkoxy, $—NH_2$, $—N(CH_3)_2$, —C(=O)OH, trifluoromethyl, —C≡N, $—C(=O)O(C_1\text{-}C_4)$alkyl, $—C(=O)NH_2$, $—SO_2NH_2$, $—C(=NH)NH_2$, and $—NO_2$, preferably containing one or two substituents selected from halogen, —OH, alkoxy, $—NH_2$, trifluoromethyl, $—N(CH_3)_2$, and —C(=)OH, more preferably selected from halogen, alkoxy and —OH. Examples of substituted alkyls include, but are not limited to, 2,2-difluoropropyl, 2-carboxycyclopentyl and 3-chloropropyl.

As used herein, the term "heteroalkyl" by itself or in combination with another term means, unless otherwise stated, a stable straight or branched chain alkyl group consisting of the stated number of carbon atoms and one or two heteroatoms selected from the group consisting of O, N, and S, and wherein the nitrogen and sulfur atoms may be optionally oxidized and the nitrogen heteroatom may be optionally quaternized. The heteroatom(s) may be placed at any position of the heteroalkyl group, including between the rest of the heteroalkyl group and the fragment to which it is attached, as well as attached to the most distal carbon atom in the heteroalkyl group. Examples include: $—OCH_2CH_2CH_3$, $—CH_2CH_2CH_2OH$, $—CH_2CH_2NHCH_3$, $—CH_2SCH_2CH_3$, and $—CH_2CH_2S(=O)CH_3$. Up to two heteroatoms may be consecutive, such as, for example, $—CH_2NHOCH_3$, or $—CH_2CH_2SSCH_3$ As used herein, the term "alkoxy" employed alone or in combination with other terms means, unless otherwise stated, an alkyl group having the designated number of carbon atoms, as defined above, connected to the rest of the molecule via an oxygen atom, such as, for example, methoxy, ethoxy, 1-propoxy, 2-propoxy (isopropoxy) and the higher homologs and isomers. Preferred are $(C_1\text{-}C_3)$ alkoxy, particularly ethoxy and methoxy.

As used herein, the term "halo" or "halogen" alone or as part of another substituent means, unless otherwise stated, a fluorine, chlorine, bromine, or iodine atom, preferably, fluorine, chlorine, or bromine, more preferably, fluorine or chlorine.

As used herein, the term "cycloalkyl" refers to a mono cyclic or polycyclic non-aromatic radical, wherein each of the atoms forming the ring (i.e. skeletal atoms) is a carbon atom. In certain embodiments, the cycloalkyl group is saturated or partially unsaturated. In other embodiments, the cycloalkyl group is fused with an aromatic ring. Cycloalkyl groups include groups having from 3 to 10 ring atoms. Illustrative examples of cycloalkyl groups include, but are not limited to, the following moieties:

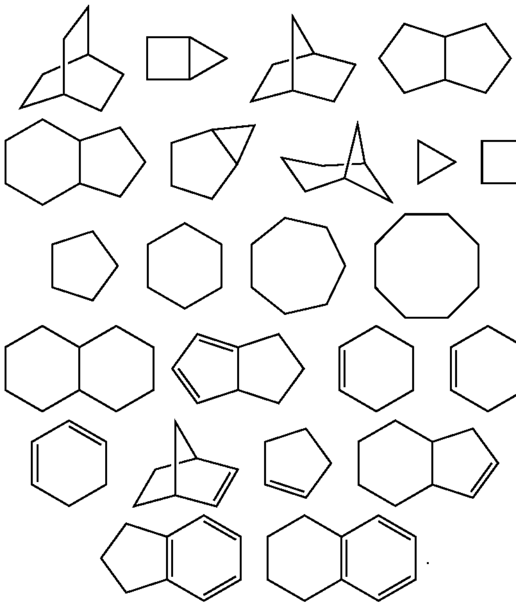

Monocyclic cycloalkyls include, but are not limited to, cyclopropyl, cyclobutyl, cyclopentyl, cyclohexyl, cycloheptyl, and cyclooctyl. Dicyclic cycloalkyls include, but are not limited to, tetrahydronaphthyl, indanyl, and tetrahydropentalene. Polycyclic cycloalkyls include adamantine and norbornane. The term cycloalkyl includes "unsaturated nonaromatic carbocyclyl" or "nonaromatic unsaturated carbocyclyl" groups, both of which refer to a nonaromatic carbocycle as defined herein, which contains at least one carbon carbon double bond or one carbon carbon triple bond.

As used herein, the term "heterocycloalkyl" or "heterocyclyl" refers to a heteroalicyclic group containing one to four ring heteroatoms each selected from O, S and N. In certain embodiments, each heterocycloalkyl group has from 4 to 10 atoms in its ring system, with the proviso that the ring of said group does not contain two adjacent O or S atoms. In other embodiments, the heterocycloalkyl group is fused with an aromatic ring. In certain embodiments, the nitrogen and sulfur heteroatoms may be optionally oxidized, and the nitrogen atom may be optionally quaternized. The heterocyclic system may be attached, unless otherwise stated, at any heteroatom or carbon atom that affords a stable structure. A heterocycle may be aromatic or non-aromatic in nature. In certain embodiments, the heterocycle is a heteroaryl.

An example of a 3-membered heterocycloalkyl group includes, and is not limited to, aziridine. Examples of 4-membered heterocycloalkyl groups include, and are not limited to, azetidine and a beta lactam. Examples of 5-membered heterocycloalkyl groups include, and are not limited to, pyrrolidine, oxazolidine and thiazolidinedione. Examples of 6-membered heterocycloalkyl groups include, and are not limited to, piperidine, morpholine and piperazine. Other non-limiting examples of heterocycloalkyl groups are:

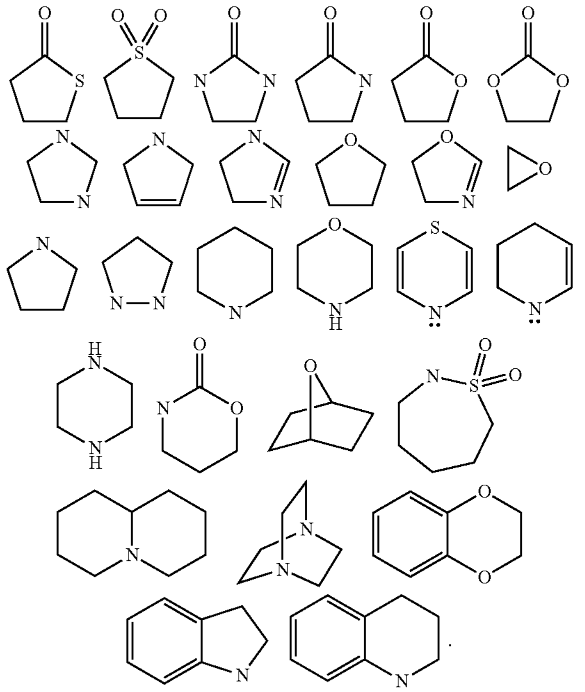

Examples of non-aromatic heterocycles include monocyclic groups such as aziridine, oxirane, thiirane, azetidine, oxetane, thietane, pyrrolidine, pyrroline, pyrazolidine, imidazoline, dioxolane, sulfolane, 2,3-dihydrofuran, 2,5-dihydrofuran, tetrahydrofuran, thiophane, piperidine, 1,2,3,6-tetrahydropyridine, 1,4-dihydropyridine, piperazine, morpholine, thiomorpholine, pyran, 2,3-dihydropyran, tetrahydropyran, 1,4-dioxane, 1,3-dioxane, homopiperazine, homopiperidine, 1,3-dioxepane, 4,7-dihydro-1,3-dioxepin, and hexamethyleneoxide.

As used herein, the term “aromatic” refers to a carbocycle or heterocycle with one or more polyunsaturated rings and having aromatic character, i.e. having (4n+2) delocalized π (pi) electrons, where n is an integer.

As used herein, the term “aryl,” employed alone or in combination with other terms, means, unless otherwise stated, a carbocyclic aromatic system containing one or more rings (typically one, two or three rings), wherein such rings may be attached together in a pendent manner, such as a biphenyl, or may be fused, such as naphthalene. Examples of aryl groups include phenyl, anthracyl, and naphthyl. Preferred examples are phenyl and naphthyl, most preferred is phenyl.

As used herein, the term “aryl-($C_1$-$C_3$)alkyl” means a functional group wherein a one- to three-carbon alkylene chain is attached to an aryl group, e.g., —$CH_2CH_2$-phenyl. Preferred is aryl-$CH_2$— and aryl-$CH(CH_3)$—. The term “substituted aryl-($C_1$-$C_3$)alkyl” means an aryl-($C_1$-$C_3$)alkyl functional group in which the aryl group is substituted. Preferred is substituted aryl($CH_2$)—. Similarly, the term “heteroaryl-($C_1$-$C_3$)alkyl” means a functional group wherein a one to three carbon alkylene chain is attached to a heteroaryl group, e.g., —$CH_2CH_2$-pyridyl. Preferred is heteroaryl-($CH_2$)—. The term “substituted heteroaryl-($C_1$-$C_3$) alkyl” means a heteroaryl-($C_1$-$C_3$)alkyl functional group in which the heteroaryl group is substituted. Preferred is substituted heteroaryl-($CH_2$)—.

As used herein, the term “heteroaryl” or “heteroaromatic” refers to a heterocycle having aromatic character. A polycyclic heteroaryl may include one or more rings that are partially saturated. Examples include the following moieties:

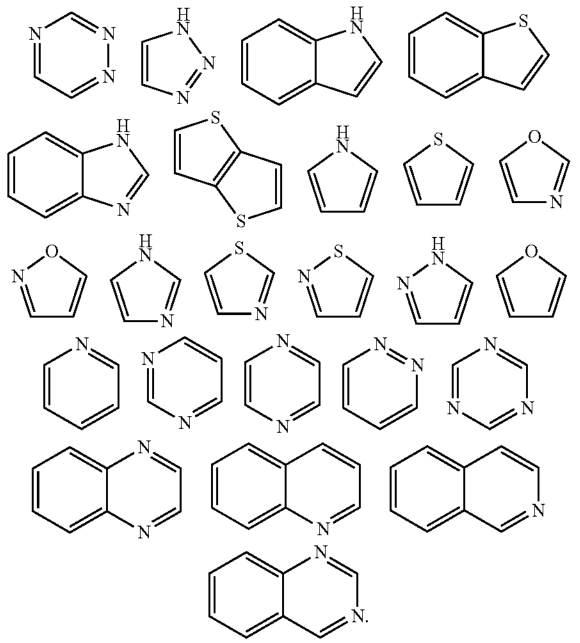

Examples of heteroaryl groups also include pyridyl, pyrazinyl, pyrimidinyl (particularly 2- and 4-pyrimidinyl), pyridazinyl, thienyl, furyl, pyrrolyl (particularly 2-pyrrolyl), imidazolyl, thiazolyl, oxazolyl, pyrazolyl (particularly 3- and 5-pyrazolyl), isothiazolyl, 1,2,3-triazolyl, 1,2,4-triazolyl, 1,3,4-triazolyl, tetrazolyl, 1,2,3-thiadiazolyl, 1,2,3-oxadiazolyl, 1,3,4-thiadiazolyl and 1,3,4-oxadiazolyl.

Examples of polycyclic heterocycles and heteroaryls include indolyl (particularly 3-, 4-, 5-, 6- and 7-indolyl), indolinyl, quinolyl, tetrahydroquinolyl, isoquinolyl (particularly 1- and 5-isoquinolyl), 1,2,3,4-tetrahydroisoquinolyl, cinnolinyl, quinoxalinyl (particularly 2- and 5-quinoxalinyl), quinazolinyl, phthalazinyl, 1,8-naphthyridinyl, 1,4-benzodioxanyl, coumarin, dihydrocoumarin, 1,5-naphthyridinyl, benzofuryl (particularly 3-, 4-, 5-, 6- and 7-benzofuryl), 2,3-dihydrobenzofuryl, 1,2-benzisoxazolyl, benzothienyl (particularly 3-, 4-, 5-, 6-, and 7-benzothienyl), benzoxazolyl, benzothiazolyl (particularly 2-benzothiazolyl and 5-benzothiazolyl), purinyl, benzimidazolyl (particularly 2-benzimidazolyl), benzotriazolyl, thioxanthinyl, carbazolyl, carbolinyl, acridinyl, pyrrolizidinyl, and quinolizidinyl.

As used herein, the term “substituted” means that an atom or group of atoms has replaced hydrogen as the substituent attached to another group. The term “substituted” further refers to any level of substitution, namely mono-, di-, tri-, tetra-, or penta-substitution, where such substitution is permitted. The substituents are independently selected, and substitution may be at any chemically accessible position. In certain embodiments, the substituents vary in number between one and four. In other embodiments, the substituents vary in number between one and three. In yet other embodiments, the substituents vary in number between one and two.

As used herein, the term "optionally substituted" means that the referenced group may be substituted or unsubstituted. In certain embodiments, the referenced group is optionally substituted with zero substituents, i.e., the referenced group is unsubstituted. In other embodiments, the referenced group is optionally substituted with one or more additional group(s) individually and independently selected from groups described herein.

In certain embodiments, the substituents are independently selected from the group consisting of oxo, halogen, —CN, —$NH_2$, —OH, —$NH(CH_3)$, —$N(CH_3)_2$, alkyl (including straight chain, branched and/or unsaturated alkyl), substituted or unsubstituted cycloalkyl, substituted or unsubstituted heterocycloalkyl, fluoro alkyl, substituted or unsubstituted heteroalkyl, substituted or unsubstituted alkoxy, fluoroalkoxy, —S-alkyl, $S(=O)_2$alkyl, —C(=O)NH[substituted or unsubstituted alkyl, or substituted or unsubstituted phenyl], —C(=O)N[H or alkyl]$_2$, —OC(=O)N[substituted or unsubstituted alkyl]$_2$, —NHC(=O)NH [substituted or unsubstituted alkyl, or substituted or unsubstituted phenyl], —NHC(=O)alkyl, —N[substituted or unsubstituted alkyl]C(=O)[substituted or unsubstituted alkyl], —NHC(=O)[substituted or unsubstituted alkyl], —C(OH)[substituted or unsubstituted alkyl]$_2$, and —C($NH_2$)[substituted or unsubstituted alkyl]$_2$. In other embodiments, by way of example, an optional substituent is selected from oxo, fluorine, chlorine, bromine, iodine, —CN, —$NH_2$, —OH, —$NH(CH_3)$, —$N(CH_3)_2$, —$CH_3$, —$CH_2CH_3$, —$CH(CH_3)_2$, —$CF_3$, —$CH_2CF_3$, —$OCH_3$, —$OCH_2CH_3$, —$OCH(CH_3)_2$, —$OCF_3$, —$OCH_2CF_3$, —$S(=O)_2$—$CH_3$, —C(=O)$NH_2$, —C(—O)—$NHCH_3$, —NHC(=O)$NHCH_3$, —C(=O)$CH_3$, and —C(=O)OH. In yet one embodiment, the substituents are independently selected from the group consisting of $C_{1-6}$ alkyl, —OH, $C_{1-6}$ alkoxy, halo, amino, acetamido, oxo and nitro. In yet other embodiments, the substituents are independently selected from the group consisting of $C_{1-6}$ alkyl, $C_{1-6}$ alkoxy, halo, acetamido, and nitro. As used herein, where a substituent is an alkyl or alkoxy group, the carbon chain may be branched, straight or cyclic, with straight being preferred.

As used herein, the term "CT110" or "CT189" refers to 1-(4-chlorophenyl)-3-(3-(4-fluorophenoxy)-prop-1-yl)guanidine).

As used herein, the term "CT360" refers to methyl 6-(3-(2,2-dimethyl-3-(4-(trifluoromethyl)phenoxy)propyl) guanidino)nicotinate.

As used herein, the term "CT1107" refers to 1-(5-cyano-4-methoxypyridin-2-yl)-3-(3-methyl-3-(4-(trifluoromethyl) phenyl)butyl)guanidine.

As used herein, the term "haloperidol" or "Hal" refers to 4-[4-(4-chlorophenyl)-4-hydroxypiperidin-1-yl]-1-(4-fluorophenyl)butan-1-one.

As used herein, the term "IPAG" refers to 1-(4-iodophenyl)-3-(2-adamantyl)guanidine.

As used herein, the term "PRE084" refers to 2-morpholin-4-ylethyl 1-phenylcyclohexane-1-carboxylate.

As used herein, the term "S1RA" refers to 4-[2-[[5-methyl-1-(2-naphthalenyl)-1H-pyrazol-3-yl]oxy]ethyl]morpholine.

As used herein, the term "SA4503" refers to 1-(3,4-dimethoxyphenethyl)-4-(3-phenylpropyl) piperazine.

Ranges: throughout this disclosure, various aspects of the disclosure can be presented in a range format. It should be understood that the description in range format is merely for convenience and brevity and should not be construed as an inflexible limitation on the scope of the disclosure. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Compounds

The compounds contemplated within the disclosure may be synthesized using techniques well-known in the art of organic synthesis. The starting materials and intermediates required for the synthesis may be obtained from commercial sources or synthesized according to methods known to those skilled in the art.

In one aspect, the compound contemplated within the disclosure is a compound of formula (I), or a salt, solvate, enantiomer, diastereoisomer, tautomer, or N-oxide thereof:

(I)

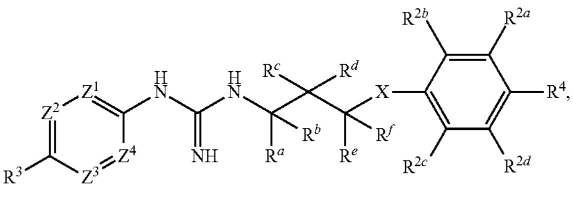

wherein:

one of the following applies:

| | | | |
|---|---|---|---|
| (a) $Z^1$ is $CR^{1a}$; | $Z^2$ is N; | $Z^3$ is $CR^{1c}$ or N; | $Z^4$ is $CR^{1d}$; |
| (b) $Z^1$ is N; | $Z^2$ is $CR^{1b}$; | $Z^3$ is $CR^{1c}$; | $Z^4$ is $CR^{1d}$ or N; |
| (c) $Z^1$ is $CR^{1a}$; | $Z^2$ is N; | $Z^3$ is $CR^{1c}$; | $Z^4$ is N; |
| (d) $Z^1$ is N; | $Z^2$ is $CR^{1b}$; | $Z^3$ is N; | $Z^4$ is $CR^{1d}$; |

X is selected from the group consisting of bond and O;

each occurrence of $R^{1a}$, $R^{1b}$, $R^{1c}$, and $R^{1d}$ is independently selected from the group consisting of $C_1$-$C_6$ alkyl, $C_1$-$C_6$ fluoroalkyl, $C_1$-$C_6$ heteroalkyl, F, Cl, Br, I, —CN, —$NO_2$, —$OR^5$, —$SR^5$, —S(=O)$R^5$, —$S(=O)_2$ $R^5$, —NHS(=O)$_2R^5$, —C(=O)$R^5$, —OC(=O)$R^5$, —$CO_2R^5$, —$OCO_2R^5$, —$CH(R^5)_2$, —N$(R^5)_2$, —C(=O)N$(R^5)_2$, —OC(=O)N$(R^5)_2$, —NHC(=O)NH$(R^5)$, —NHC(=O)$R^5$, —NHC(=O)O$R^5$, —C(OH)$(R^5)_2$, and —C($NH_2$)$(R^5)_2$;

each occurrence of $R^{2a}$, $R^{2b}$, $R^{2c}$, and $R^{2d}$ is independently selected from the group consisting of $C_1$-$C_6$ alkyl, $C_1$-$C_6$ fluoroalkyl, $C_1$-$C_6$ heteroalkyl, F, Cl, Br, I, —CN, —$NO_2$, —$OR^5$, —$SR^5$, —S(=O)$R^5$, —$S(=O)_2$ $R^5$, —NHS(=O)$_2R^5$, —C(=O)$R^5$, —OC(=O)$R^5$, —$CO_2R^5$, —$OCO_2R^5$, —$CH(R^5)_2$, —N$(R^5)_2$, —C(=O)N$(R^5)_2$, —OC(=O)N$(R^5)_2$, —NHC (=O)NH($R^5$), —NHC(=O)$R^5$, —NHC(=O)O$R^5$, —C(OH)($R^5$)$_2$, and —C($NH_2$)($R^5$)$_2$;

$R^3$ is selected from the group consisting of CN, F, Cl, Br, I, $C_1$-$C_6$ haloalkyl, $C_1$-$C_6$ haloalkoxy, and —C(O)O$R^6$;

$R^4$ is selected from the group consisting of CN, F, Cl, Br, I, $C_1$-$C_6$ haloalkyl, $C_1$-$C_6$ haloalkoxy, and —C(O)O$R^7$;

each occurrence of $R^5$ is independently selected from the group consisting of H, $C_1$-$C_6$ alkyl, $C_1$-$C_6$ heteroalkyl, aryl, and —$C_1$-$C_3$ alkyl-($C_3$-$C_6$ cycloalkyl), wherein the alkyl, heteroalkyl, aryl, or cycloalkyl group is optionally substituted;

$R^6$ is selected from the group consisting of H, $C_1$-$C_6$ alkyl, $C_1$-$C_6$ heteroalkyl, and $C_3$-$C_6$ cycloalkyl, wherein the alkyl, heteroalkyl, or cycloalkyl group is optionally substituted;

$R^7$ is selected from the group consisting of H, $C_1$-$C_6$ alkyl, $C_1$-$C_6$ heteroalkyl, and $C_3$-$C_6$ cycloalkyl, wherein the alkyl, heteroalkyl, or cycloalkyl group is optionally substituted; and each occurrence of $R^a$, $R^b$, $R^c$, $R^d$, $R^e$, and $R^f$ is independently selected from the group consisting of H and $CH_3$, with the proviso that, if Y is $CR^{1c}$ and Z is $CR^{1d}$, then at least one of $R^a$, $R^b$, $R^c$, $R^d$, $R^e$, and $R^f$ is $CH_3$.

In certain embodiments, $Z^1$ is $CR^{1a}$; $Z^2$ is N; $Z^3$ is $CR^{1c}$; $Z^4$ is $CR^{1d}$.

In certain embodiments, $Z^1$ is $CR^{1a}$; $Z^2$ is N; $Z^3$ is N; $Z^4$ is $CR^{1d}$.

In certain embodiments, $Z^1$ is N; $Z^2$ is $CR^{1b}$; $Z^3$ is $CR^{1c}$; $Z^4$ is $CR^{1d}$.

In certain embodiments, $Z^1$ is N; $Z^2$ is $CR^{1b}$; $Z^3$ is $CR^{1c}$; $Z^4$ is N.

In certain embodiments, $Z^1$ is $CR^{1a}$; $Z^2$ is N; $Z^3$ is $CR^{1c}$; $Z^4$ is N.

In certain embodiments, $Z^1$ is N; $Z^2$ is $CR^{1b}$; $Z^3$ is N; $Z^4$ is $CR^{1d}$.

In certain embodiments, X is bond. In certain embodiments, X is O.

In certain embodiments, each occurrence of $R^{1a}$, $R^{1b}$, $R^{1c}$, and $R^{1d}$ is independently selected from the group consisting of $C_1$-$C_6$ alkyl, $C_1$-$C_6$ fluoroalkyl, $C_1$-$C_6$ heteroalkyl, F, Cl, Br, I, —CN, —$NO_2$, and —O$R^5$.

In certain embodiments, each occurrence of $R^{2a}$, $R^{2b}$, $R^{2c}$, and $R^{2d}$ is independently selected from the group consisting of $C_1$-$C_6$ alkyl, $C_1$-$C_6$ fluoroalkyl, $C_1$-$C_6$ heteroalkyl, F, Cl, Br, I, —CN, —$NO_2$, and —O$R^5$.

In certain embodiments, $R^3$ is CN. In certain embodiments, $R^3$ is F. In certain embodiments, $R^3$ is Cl. In certain embodiments, $R^3$ is Br. In certain embodiments, $R^3$ is I. In certain embodiments, $R^3$ is $C_1$-$C_6$ haloalkyl. In certain embodiments, $R^3$ is —$CF_3$. In certain embodiments, $R^3$ is —$CHF_2$. In certain embodiments, $R^3$ is $C_1$-$C_6$ haloalkoxy. In certain embodiments, $R^3$ is —$OCF_3$. In certain embodiments, $R^3$ is —$OCHF_2$. In certain embodiments, $R^3$ is —C(O)O$R^6$. In certain embodiments, $R^3$ is —C(O)OH. In certain embodiments, $R^3$ is —C(O)O(optionally substituted $C_1$-$C_6$ alkyl). In certain embodiments, $R^3$ is —C(O)O(optionally substituted $C_1$-$C_6$ heteroalkyl). In certain embodiments, $R^3$ is —C(O)O(optionally substituted $C_3$-$C_6$ cycloalkyl). In certain embodiments, $R^3$ is —C(O)OMe. In certain embodiments, $R^3$ is —C(O)OEt. In certain embodiments, $R^3$ is —C(O)O(n-propyl). In certain embodiments, $R^3$ is —C(O)O(i-propyl). In certain embodiments, $R^3$ is —C(O)O(n-butyl). In certain embodiments, $R^3$ is —C(O)O(sec-butyl). In certain embodiments, $R^3$ is —C(O)O(iso-butyl). In certain embodiments, $R^3$ is —C(O)O(t-butyl).

In certain embodiments, $R^4$ is CN. In certain embodiments, $R^4$ is F. In certain embodiments, $R^4$ is Cl. In certain embodiments, $R^4$ is Br. In certain embodiments, $R^4$ is I. In certain embodiments, $R4^3$ is $C_1$-$C_6$ haloalkyl. In certain embodiments, $R^4$ is —$CF_3$. In certain embodiments, $R^4$ is —$CHF_2$. In certain embodiments, $R^4$ is $C_1$-$C_6$ haloalkoxy. In certain embodiments, $R^4$ is —$OCF_3$. In certain embodiments, $R^4$ is —$OCHF_2$. In certain embodiments, $R^4$ is —C(O)O$R^7$. In certain embodiments, $R^4$ is —C(O)OH. In certain embodiments, $R^4$ is —C(O)O(optionally substituted $C_1$-$C_6$ alkyl). In certain embodiments, $R^4$ is —C(O)O(optionally substituted $C_1$-$C_6$ heteroalkyl). In certain embodiments, $R^4$ is —C(O)O(optionally substituted $C_3$-$C_6$ cycloalkyl). In certain embodiments, $R^4$ is —C(O)OMe. In certain embodiments, $R^4$ is —C(O)OEt. In certain embodiments, $R^4$ is —C(O)O(n-propyl). In certain embodiments, $R^4$ is —C(O)O(i-propyl). In certain embodiments, $R^4$ is —C(O)O(n-butyl). In certain embodiments, $R^4$ is —C(O)O(sec-butyl). In certain embodiments, $R^4$ is —C(O)O(iso-butyl). In certain embodiments, $R^4$ is —C(O)O(t-butyl).

In certain embodiments, $R^5$ is H. In certain embodiments, $R^5$ is $C_1$-$C_6$ alkyl. In certain embodiments, $R^5$ is $C_1$-$C_6$ heteroalkyl. In certain embodiments, $R^5$ is aryl. In certain embodiments, $R^5$ is —$C_1$-$C_3$ alkyl-($C_3$-$C_6$ cycloalkyl). In certain embodiments, in $R^5$ the alkyl, heteroalkyl, aryl, or cycloalkyl group is optionally substituted.

In certain embodiments, $R^a$ is H. In certain embodiments, $R^a$ is $CH_3$.

In certain embodiments, $R^b$ is H. In certain embodiments, $R^b$ is $CH_3$.

In certain embodiments, $R^c$ is H. In certain embodiments, $R^c$ is $CH_3$.

In certain embodiments, $R^d$ is H. In certain embodiments, $R^d$ is $CH_3$.

In certain embodiments, $R^e$ is H. In certain embodiments, $R^e$ is $CH_3$.

In certain embodiments, $R^f$ is H. In certain embodiments, $R^f$ is $CH_3$.

In certain embodiments, the compound of formula (I) is selected from the group consisting of:

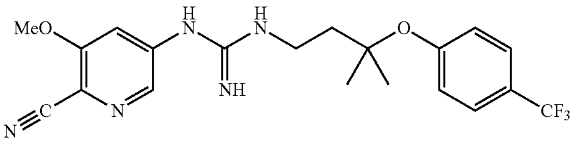 [SMILES: COc1cc(NC(=N)NCCC(C)(C)Oc2ccc(C(F)(F)F)cc2)cnc1C#N]

1-(6-cyano-5-methoxypyridin-3-yl)-3-(3-methyl-3-(4-(trifluoromethyl)phenoxy)butyl)guanidine (Compound A);

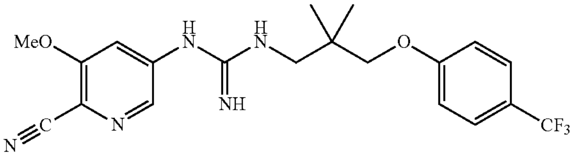 [SMILES: COc1cc(NC(=N)NCC(C)(C)COc2ccc(C(F)(F)F)cc2)cnc1C#N]

1-(6-cyano-5-methoxypyridin-3-yl)-3-(2,2-dimethyl-3-(4-(trifluoromethyl)phenoxy)propyl)guanidine (Compound B);

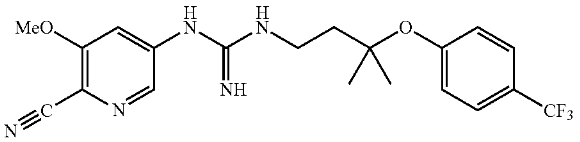 [SMILES: COc1cc(NC(=N)NCCC(C)(C)Oc2ccc(C(F)(F)F)cc2)cnc1C#N]

1-(5-cyano-4-methoxypyridin-2-yl)-3-(3-methyl-3-(4-(trifluoromethyl)phenoxy)butyl)guanidine (Compound C);

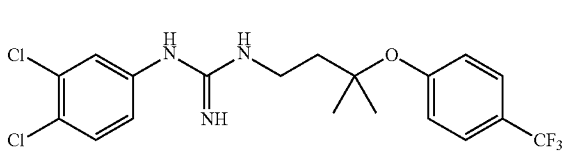 [SMILES: CC(C)(CCNC(=N)Nc1ccc(Cl)c(Cl)c1)Oc1ccc(C(F)(F)F)cc1]

1-(3,4-dichlorophenyl)-3-(3-methyl-3-(4-(trifluoromethyl)phenoxy)butyl)guanidine (Compound D);

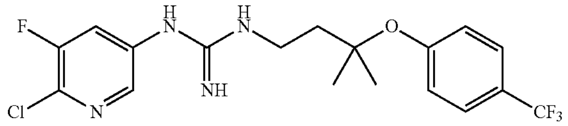

1-(6-chloro-5-fluoropyridin-3-yl)-3-(3-methyl-3-(4-(trifluoromethyl)phenoxy)butyl)guanidine (Compound E);

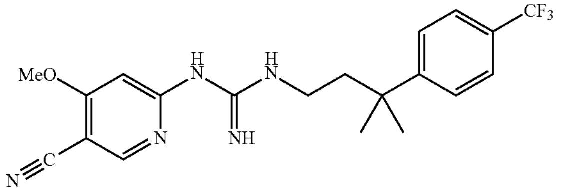 [SMILES: COc1cc(NC(=N)NCCC(C)(C)c2ccc(C(F)(F)F)cc2)ncc1C#N]

1-(5-cyano-4-methoxypyridin-2-yl)-3-(3-methyl-3-(4-(trifluoromethyl)phenyl)butyl)guanidine (Compound F);

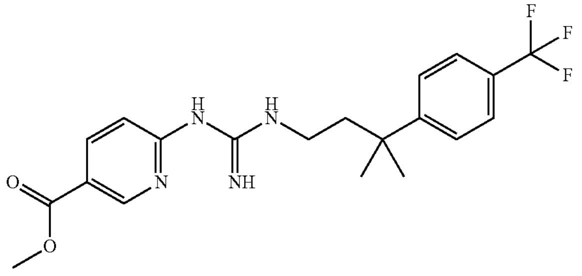 [SMILES: COC(=O)c1ccc(NC(=N)NCCC(C)(C)c2ccc(C(F)(F)F)cc2)nc1]

methyl 6-(3-(3-methyl-3-(4-(trifluoromethyl)phenyl)butyl)guanidino)nicotinate (Compound G);

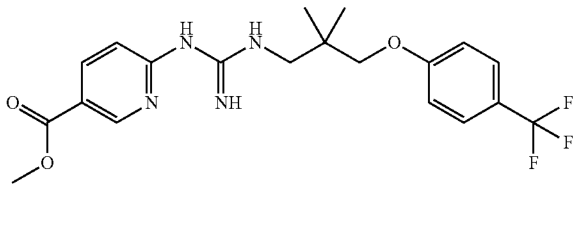 [SMILES: COC(=O)c1ccc(NC(=N)NCC(C)(C)COc2ccc(C(F)(F)F)cc2)nc1]

methyl 6-(3-(2,2-dimethyl-3-(4-(trifluoromethyl)phenoxy)propyl)guanidino)nicotinate (Compound H);

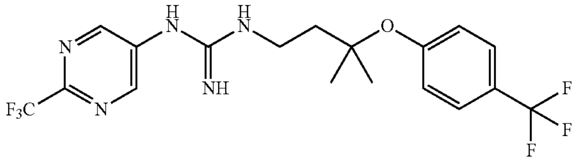 [SMILES: CC(C)(CCNC(=N)Nc1cnc(C(F)(F)F)nc1)Oc1ccc(C(F)(F)F)cc1]

1-(3-methyl-3-(4-(trifluoromethyl)phenoxy)butyl)-3-(2-(trifluoromethyl)pyrimidin-5-yl)guanidine (Compound I);

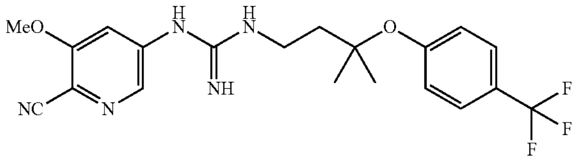 [SMILES: COc1cc(NC(=N)NCCC(C)(C)Oc2ccc(C(F)(F)F)cc2)cnc1C#N]

1-(6-cyano-5-methoxypyridin-3-yl)-3-(3-methyl-3-(4-(trifluoromethyl)phenoxy)butyl)guanidine (Compound J).

Selected biological data for compounds of the disclosure follow:

| Compound | Sigma1, $K_i$ (nM) | AR-LU $IC_{50}$ (μM)[a] |
|---|---|---|
| A | 9 | 8.1 |
| B | 6 | 10 |
| C | 14 | 1 |
| D | 8 | 3 |
| E | 5 | 5 |
| F | 11 | 3 |
| G | 3 | 2.8 |
| H | 18 | 2.9 |
| I | 35 | 10.5 |
| J | 7 | 8.5 |

[a]Androgen Receptor Transcriptional Activity as determined by AR-luciferase reporter assay

Preparation of the Compounds

Compounds contemplated within the disclosure may be prepared by the general schemes described herein, using the synthetic method known by those skilled in the art. The following examples illustrate non-limiting embodiments of the disclosure.

In a non-limiting embodiment, the synthesis of unsymmetrical N,N'-disubstituted guanidines is accomplished by coupling an aryl cyanamide and an amine. In certain embodiments, the coupling reaction takes place at an elevated temperature ranging from 80° C. to 250° C. An aniline may be converted to an aryl cyanamide with cyanogen bromide in ether. The unsymmetrical N,N'-disubstituted guanidine is then formed by coupling the aryl cyanamide with an amine. Non-limiting examples of coupling methods include heating in acetonitrile at reflux, and heating at 120° C. in a microwave.

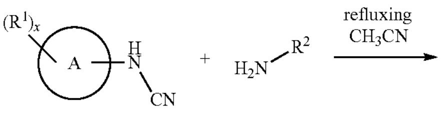

-continued

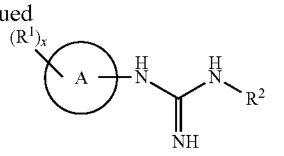

In another non-limiting embodiment, unsymmetrical N,N'-disubstituted guanidines may be synthesized by coupling a benzimidothioate and an amine. For example, an aniline may be reacted with potassium isothiocyanate to provide a thiourea. The thiourea may then be treated with methyl iodide in acetone heated to reflux, providing the desired benzimidothioate. The unsymmetrical N,N'-disubstituted guanidine may then be formed by coupling the benzimidothioate with an amine. A non-limiting example of a coupling method includes heating in ethanol at reflux.

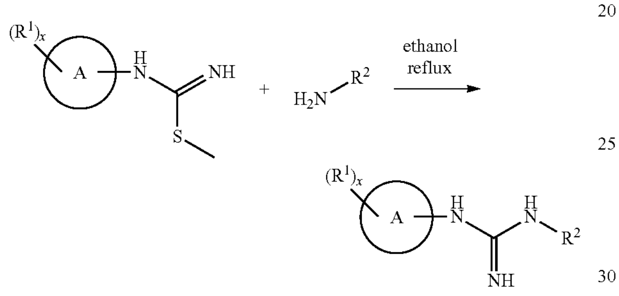

The compounds of the disclosure may possess one or more stereocenters, and each stereocenter may exist independently in either the R or S configuration. In certain embodiments, compounds described herein are present in optically active or racemic forms. It is to be understood that the compounds described herein encompass racemic, optically-active, regioisomeric and stereoisomeric forms, or combinations thereof that possess the therapeutically useful properties described herein. Preparation of optically active forms is achieved in any suitable manner, including by way of non-limiting example, by resolution of the racemic form with recrystallization techniques, synthesis from optically-active starting materials, chiral synthesis, or chromatographic separation using a chiral stationary phase. In certain embodiments, a mixture of one or more isomer is utilized as the therapeutic compound described herein. In other embodiments, compounds described herein contain one or more chiral centers. These compounds are prepared by any means, including stereoselective synthesis, enantioselective synthesis and/or separation of a mixture of enantiomers and/or diastereomers. Resolution of compounds and isomers thereof is achieved by any means including, by way of non-limiting example, chemical processes, enzymatic processes, fractional crystallization, distillation, and chromatography.

The methods and formulations described herein include the use of N-oxides (if appropriate), crystalline forms (also known as polymorphs), solvates, amorphous phases, and/or pharmaceutically acceptable salts of compounds having the structure of any compound of the disclosure, as well as metabolites and active metabolites of these compounds having the same type of activity. Solvates include water, ether (e.g., tetrahydrofuran, methyl tert-butyl ether) or alcohol (e.g., ethanol) solvates, acetates and the like. In certain embodiments, the compounds described herein exist in solvated forms with pharmaceutically acceptable solvents such as water, and ethanol. In other embodiments, the compounds described herein exist in unsolvated form.

In certain embodiments, the compounds of the disclosure may exist as tautomers. All tautomers are included within the scope of the compounds presented herein.

In certain embodiments, compounds described herein are prepared as prodrugs. A "prodrug" refers to an agent that is converted into the parent drug in vivo. In certain embodiments, upon in vivo administration, a prodrug is chemically converted to the biologically, pharmaceutically or therapeutically active form of the compound. In other embodiments, a prodrug is enzymatically metabolized by one or more steps or processes to the biologically, pharmaceutically or therapeutically active form of the compound.

In certain embodiments, sites on, for example, the aromatic ring portion of compounds of the disclosure are susceptible to various metabolic reactions. Incorporation of appropriate substituents on the aromatic ring structures may reduce, minimize or eliminate this metabolic pathway. In certain embodiments, the appropriate substituent to decrease or eliminate the susceptibility of the aromatic ring to metabolic reactions is, by way of example only, a deuterium, a halogen, or an alkyl group.

Compounds described herein also include isotopically-labeled compounds wherein one or more atoms is replaced by an atom having the same atomic number, but an atomic mass or mass number different from the atomic mass or mass number usually found in nature. Examples of isotopes suitable for inclusion in the compounds described herein include and are not limited to $^{2}H$, $^{3}H$, $^{11}C$, $^{13}C$, $^{14}C$, $^{36}Cl$, $^{18}F$, $^{123}I$, $^{125}I$, $^{13}N$, $^{15}N$, $^{15}O$, $^{17}O$, $^{18}O$, $^{32}P$, and $^{35}S$. In certain embodiments, isotopically-labeled compounds are useful in drug and/or substrate tissue distribution studies. In other embodiments, substitution with heavier isotopes such as deuterium affords greater metabolic stability (for example, increased in vivo half-life or reduced dosage requirements). In yet other embodiments, substitution with positron emitting isotopes, such as $^{11}C$, $^{18}F$, $^{15}O$ and $^{13}N$, is useful in Positron Emission Topography (PET) studies for examining substrate receptor occupancy. Isotopically-labeled compounds are prepared by any suitable method or by processes using an appropriate isotopically-labeled reagent in place of the non-labeled reagent otherwise employed.

In certain embodiments, the compounds described herein are labeled by other means, including, but not limited to, the use of chromophores or fluorescent moieties, bioluminescent labels, or chemiluminescent labels.

The compounds described herein, and other related compounds having different substituents are synthesized using techniques and materials described herein and as described, for example, in Fieser & Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), Larock's Comprehensive Organic Transformations (VCH Publishers Inc., 1989), March, Advanced Organic Chemistry $4^{th}$ Ed., (Wiley 1992); Carey & Sundberg, Advanced Organic Chemistry 4th Ed., Vols. A and B (Plenum 2000, 2001), and Green & Wuts, Protective Groups in Organic Synthesis 3rd Ed., (Wiley 1999) (all of which are incorporated by reference for such disclosure). General methods for the preparation of compound as described herein are modified by the use of appropriate reagents and conditions, for the introduction of the various moieties found in the formula as provided herein.

Compounds described herein are synthesized using any suitable procedures starting from compounds that are available from commercial sources, or are prepared using procedures described herein.

In certain embodiments, reactive functional groups, such as hydroxyl, amino, imino, thio or carboxy groups, are protected in order to avoid their unwanted participation in reactions. Protecting groups are used to block some or all of the reactive moieties and prevent such groups from participating in chemical reactions until the protective group is removed. In other embodiments, each protective group is removable by a different means. Protective groups that are cleaved under totally disparate reaction conditions fulfill the requirement of differential removal.

In certain embodiments, protective groups are removed by acid, base, reducing conditions (such as, for example, hydrogenolysis), and/or oxidative conditions. Groups such as trityl, dimethoxytrityl, acetal and t-butyldimethylsilyl are acid labile and are used to protect carboxy and hydroxy reactive moieties in the presence of amino groups protected with Cbz groups, which are removable by hydrogenolysis, and Fmoc groups, which are base labile. Carboxylic acid and hydroxy reactive moieties are blocked with base labile groups such as, but not limited to, methyl, ethyl, and acetyl, in the presence of amines that are blocked with acid labile groups, such as t-butyl carbamate, or with carbamates that are both acid and base stable but hydrolytically removable.

In certain embodiments, carboxylic acid and hydroxy reactive moieties are blocked with hydrolytically removable protective groups such as the benzyl group, while amine groups capable of hydrogen bonding with acids are blocked with base labile groups such as Fmoc. Carboxylic acid reactive moieties are protected by conversion to simple ester compounds as exemplified herein, which include conversion to alkyl esters, or are blocked with oxidatively-removable protective groups such as 2,4-dimethoxybenzyl, while co-existing amino groups are blocked with fluoride labile silyl carbamates.

Allyl blocking groups are useful in the presence of acid- and base-protecting groups since the former are stable and are subsequently removed by metal or pi-acid catalysts. For example, an allyl-blocked carboxylic acid is deprotected with a palladium-catalyzed reaction in the presence of acid labile t-butyl carbamate or base-labile acetate amine protecting groups. Yet another form of protecting group is a resin to which a compound or intermediate is attached. As long as the residue is attached to the resin, that functional group is blocked and does not react. Once released from the resin, the functional group is available to react.

Typically blocking/protecting groups may be selected from:

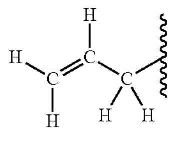

allyl

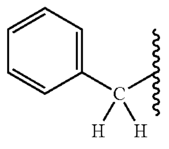

Bn

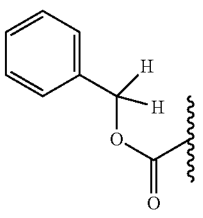

Cbz

-continued

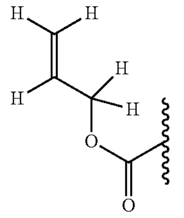

Alloc

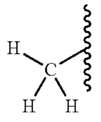

Me

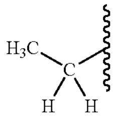

Et

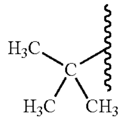

t-butyl

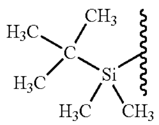

TBDMS

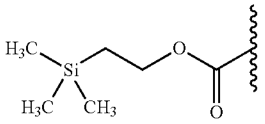

Teoc

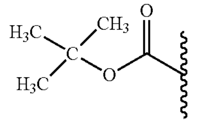

Boc

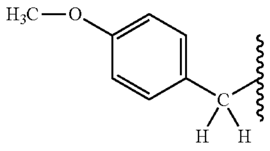

PMB

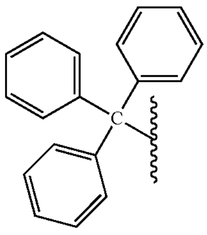

trityl

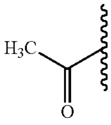

acetyl

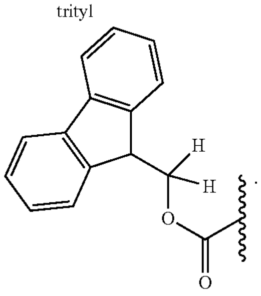

FMOC

Other protecting groups, plus a detailed description of techniques applicable to the creation of protecting groups and their removal are described in Greene & Wuts, Protective Groups in Organic Synthesis, 3rd Ed., John Wiley & Sons, New York, NY, 1999, and Kocienski, Protective Groups, Thieme Verlag, New York, NY, 1994, which are incorporated herein by reference for such disclosure.

Methods

The disclosure includes a method of disrupting viral lifecycle, infection, and/or dissemination in a virus-infected subject, and/or preventing or minimizing virus infection and/or dissemination in a subject, wherein the virus comprises at least one surface viral protein that is involved in viral entry and/or viral infection. The disclosure further includes a method of inhibiting, minimizing, and/or preventing formation of virus particles in a virus-infected subject, wherein the virus comprises at least one surface viral protein that is involved in viral entry and/or viral infection. The disclosure further includes a method of altering production, post-translational modification, assembly, maturation, and/or functional cell surface expression of at least one virus protein involved in viral entry and/or viral infection in a subject's cell. The disclosure further includes a method of initiating or stimulating selective autophagosomal, lysosomal, and/or proteasomal degradation of at least one virus protein involved in viral entry and/or viral infection in a subject's cell. The disclosure further includes a method of decreasing or inhibiting increase of amount, concentration, and/or production of at least one virus protein involved in viral entry and/or viral infection in a subject's cell. The disclosure further includes a method of altering and/or disturbing subcellular localization and/or virus promoting activity of at least one virus protein involved in viral entry and/or viral infection in a subject's cell. The disclosure further includes a method of minimizing and/or preventing a surface viral protein incorporation into a virion in a virus-infected eukaryotic cell.

The disclosure further includes a method of promoting autophagic degradation of NSP6 in a coronavirus-infected eukaryotic cell. The disclosure further includes a method of decreasing or inhibiting increase of NSP6 concentration in a coronavirus-infected eukaryotic cell. The disclosure further includes a method of minimizing and/or suppressing TMPRSS2 protein levels and cell surface localization on an eukaryotic cell.

In certain embodiments, the virus comprises a flavivirus. In other embodiments, the flavivirus comprises at least one of Zika virus, Dengue virus, and Powassan virus. In yet other embodiments, the flavivirus comprises at least one of Apoi virus, Aroa virus, Bamaga virus, Bagaza virus, Banzi virus, Bouboui virus, Bukalasa bat virus, Cacipacore virus, Carey Island virus, Cowbone Ridge virus, Dakar bat virus, Dengue virus, Edge Hill virus, Entebbe bat virus, Gadgets Gully virus, Ilheus virus, Israel turkey meningoencephalomyelitis virus, Japanese encephalitis virus, Jugra virus, Jutiapa virus, Kadam virus, Kedougou virus, Kokobera virus, Koutango virus, Kyasanur Forest disease virus, Langat virus, Louping ill virus, Meaban virus, Modoc virus, Montana myotis leukoencephalitis virus, Murray Valley encephalitis virus, Ntaya virus, Omsk hemorrhagic fever virus, Phnom Penh bat virus, Powassan virus, Rio Bravo virus, Royal Farm virus, Saboya virus, Saint Louis encephalitis virus, Sal Vieja virus, San Perlita virus, Saumarez Reef virus, Sepik virus, Tembusu virus, Tick-borne encephalitis virus, Tyuleniy virus, Uganda S virus, Usutu virus, Wesselsbron virus, West Nile virus, Yaounde virus, Yellow fever virus, Yokose virus, and Zika virus.

In certain embodiments, the virus comprises a Coronavirus. In other embodiments, the Coronavirus comprises at least one of an Alphacoronavirus, a Betacoronavirus, a Gammacoronavirus, and a Deltacoronavirus. In yet other embodiments, the Coronavirus comprises at least one of MERS-CoV, SARS-CoV, and SARS-CoV-2, and any variants thereof. In certain embodiments, the virus comprises a coronavirus and the surface viral protein comprises a Spike (S) protein.

In certain embodiments, the method comprises administering to the subject an effective amount of at least one compound contemplated within the disclosure. In other embodiments, the subject is further administered at least one additional antiviral agent and/or at least one additional agent that treats, ameliorates, and/or prevents one or more virus infection symptoms and/or co-morbidities. In yet other embodiments, the compound and the at least one additional agent are co-administered to the subject. In yet other embodiments, the compound and the at least one additional agent are co-formulated.

In certain embodiments, the subject is a mammal. In other embodiments, the mammal is a human.

Combination Therapies

The compounds contemplated within the disclosure are intended to be useful in combination with one or more additional compounds. These additional compounds may comprise compounds of the present disclosure and/or at least one additional antiviral agent and/or at least one additional agent that treats one or more coronavirus infection symptoms and/or co-morbidities.

A synergistic effect may be calculated, for example, using suitable methods such as, for example, the Sigmoid-$E_{max}$ equation (Holford & Scheiner, 1981, Clin. Pharmacokinet. 6:429-453), the equation of Loewe additivity (Loewe & Muischnek, 1926, Arch. Exp. Pathol Pharmacol. 114:313-326) and the median-effect equation (Chou & Talalay, 1984, Adv. Enzyme Regul. 22:27-55). Each equation referred to above may be applied to experimental data to generate a corresponding graph to aid in assessing the effects of the drug combination. The corresponding graphs associated with the equations referred to above are the concentration-effect curve, isobologram curve and combination index curve, respectively.

Administration/Dosage/Formulations

The regimen of administration may affect what constitutes an effective amount. The therapeutic formulations contemplated within the disclosure may be administered to the subject either prior to or after the onset of a coronavirus infection. Further, several divided dosages, as well as staggered dosages may be administered daily or sequentially, or the dose may be continuously infused, or may be a bolus injection. Further, the dosages of the therapeutic formulations contemplated within the disclosure may be proportionally increased or decreased as indicated by the exigencies of the therapeutic or prophylactic situation.

Administration of the compositions contemplated within the disclosure to a patient, preferably a mammal, more preferably a human, may be carried out using known procedures, at dosages and for periods of time effective to treat a coronavirus infection in the patient. An effective amount of the therapeutic compound necessary to achieve a therapeutic effect may vary according to factors such as the state of the disease or disorder in the patient; the age, sex, and weight of the patient; and the ability of the therapeutic compound contemplated within the disclosure to treat a coronavirus infection in the patient. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic compound contemplated within the disclosure is from about 1 and 5,000 mg/kg of body weight/per day. One of ordinary skill in the art would be able to study the relevant factors and make the determination regarding the effective amount of the therapeutic compound without undue experimentation.

Actual dosage levels of the active ingredients in the pharmaceutical compositions contemplated within the disclosure may be varied so as to obtain an amount of the active ingredient that is effective to achieve the desired therapeutic response for a particular patient, composition, and mode of administration, without being toxic to the patient.

In particular, the selected dosage level depends upon a variety of factors including the activity of the particular compound employed, the time of administration, the rate of excretion of the compound, the duration of the treatment, other drugs, compounds or materials used in combination with the compound, the age, sex, weight, condition, general health and prior medical history of the patient being treated, and like factors well, known in the medical arts.

A medical doctor, e.g., physician or veterinarian, having ordinary skill in the art may readily determine and prescribe the effective amount of the pharmaceutical composition required. For example, the physician or veterinarian could start doses of the compounds contemplated within the disclosure employed in the pharmaceutical composition at levels lower than that required in order to achieve the desired therapeutic effect and gradually increase the dosage until the desired effect is achieved.

In particular embodiments, it is especially advantageous to formulate the compound in dosage unit form for ease of administration and uniformity of dosage. Dosage unit form as used herein refers to physically discrete units suited as unitary dosages for the patients to be treated; each unit containing a predetermined quantity of therapeutic compound calculated to produce the desired therapeutic effect in association with the required pharmaceutical vehicle. The dosage unit forms contemplated within the disclosure are dictated by and directly dependent on (a) the unique characteristics of the therapeutic compound and the particular therapeutic effect to be achieved, and (b) the limitations inherent in the art of compounding/formulating such a therapeutic compound for the treatment of a coronavirus infection in a patient.

In certain embodiments, the compositions of the disclosure are formulated using one or more pharmaceutically acceptable excipients or carriers. In certain embodiments, the pharmaceutical compositions of the disclosure comprise a therapeutically effective amount of a compound of the disclosure and a pharmaceutically acceptable carrier.

The carrier may be a solvent or dispersion medium containing, for example, water, ethanol, polyol (for example, glycerol, propylene glycol, and liquid polyethylene glycol, and the like), suitable mixtures thereof, and vegetable oils. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal, and the like. In many cases, it is preferable to include isotonic agents, for example, sugars, sodium chloride, or polyalcohols such as mannitol and sorbitol, in the composition. Prolonged absorption of the injectable compositions may be brought about by including in the composition an agent which delays absorption, for example, aluminum monostearate or gelatin. In certain embodiments, the pharmaceutically acceptable carrier is not DMSO alone.

In certain embodiments, the compositions of the disclosure are administered to the patient in dosages that range from one to five times per day or more. In other embodiments, the compositions of the disclosure are administered to the patient in range of dosages that include, but are not limited to, once every day, every two, days, every three days to once a week, and once every two weeks. It is readily apparent to one skilled in the art that the frequency of administration of the various combination compositions of the disclosure varies from individual to individual depending on many factors including, but not limited to, age, disease or disorder to be treated, gender, overall health, and other factors. Thus, the disclosure should not be construed to be limited to any particular dosage regime and the precise dosage and composition to be administered to any patient is determined by the attending physical taking all other factors about the patient into account.

Compounds of the disclosure for administration may be in the range of from about 1 μg to about 10,000 mg, about 20 μg to about 9,500 mg, about 40 μg to about 9,000 mg, about 75 μg to about 8,500 mg, about 150 μg to about 7,500 mg, about 200 μg to about 7,000 mg, about 3050 μg to about 6,000 mg, about 500 μg to about 5,000 mg, about 750 μg to about 4,000 mg, about 1 mg to about 3,000 mg, about 10 mg to about 2,500 mg, about 20 mg to about 2,000 mg, about 25 mg to about 1,500 mg, about 30 mg to about 1,000 mg, about 40 mg to about 900 mg, about 50 mg to about 800 mg, about 60 mg to about 750 mg, about 70 mg to about 600 mg, about 80 mg to about 500 mg, and any and all whole or partial increments therebetween.

In some embodiments, the dose of a compound of the disclosure is from about 1 mg and about 2,500 mg. In some embodiments, a dose of a compound of the disclosure used in compositions described herein is less than about 10,000 mg, or less than about 8,000 mg, or less than about 6,000 mg, or less than about 5,000 mg, or less than about 3,000 mg, or less than about 2,000 mg, or less than about 1,000 mg, or less than about 500 mg, or less than about 200 mg, or less than about 50 mg. Similarly, in some embodiments, a dose of a second compound as described herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof.

In certain embodiments, the present disclosure is directed to a packaged pharmaceutical composition comprising a container holding a therapeutically effective amount of a compound of the disclosure, alone or in combination with a second pharmaceutical agent; and instructions for using the compound to treat, prevent, or reduce one or more symptoms of Sigma-receptor related disorders or diseases in a patient.

Formulations may be employed in admixtures with conventional excipients, i.e., pharmaceutically acceptable organic or inorganic carrier substances suitable for oral, parenteral, nasal, intravenous, subcutaneous, enteral, or any other suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents, e.g., other analgesic agents.

Routes of administration of any of the compositions of the disclosure include oral, nasal, rectal, intravaginal, parenteral, buccal, sublingual or topical. The compounds for use in the disclosure may be formulated for administration by any suitable route, such as for oral or parenteral, for example, transdermal, transmucosal (e.g., sublingual, lingual, (trans)buccal, (trans)urethral, vaginal (e.g., trans- and perivaginally), (intra)nasal and (trans)rectal), intravesical, intrapulmonary, intraduodenal, intragastrical, intrathecal, subcutaneous, intramuscular, intradermal, intra-arterial, intravenous, intrabronchial, inhalation, and topical administration.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present disclosure are not limited to the particular formulations and compositions that are described herein.

Oral Administration

For oral application, particularly suitable are tablets, dragees, liquids, drops, suppositories, or capsules, caplets and gelcaps. The compositions intended for oral use may be prepared according to any method known in the art and such compositions may contain one or more agents selected from the group consisting of inert, non-toxic pharmaceutically excipients that are suitable for the manufacture of tablets. Such excipients include, for example an inert diluent such as lactose; granulating and disintegrating agents such as cornstarch; binding agents such as starch; and lubricating agents such as magnesium stearate. The tablets may be uncoated or they may be coated by known techniques for elegance or to delay the release of the active ingredients. Formulations for oral use may also be presented as hard gelatin capsules wherein the active ingredient is mixed with an inert diluent.

For oral administration, the compounds of the disclosure may be in the form of tablets or capsules prepared by conventional means with pharmaceutically acceptable excipients such as binding agents (e.g., polyvinylpyrrolidone, hydroxypropylcellulose or hydroxypropylmethylcellulose); fillers (e.g., cornstarch, lactose, microcrystalline cellulose or calcium phosphate); lubricants (e.g., magnesium stearate, talc, or silica); disintegrates (e.g., sodium starch glycollate); or wetting agents (e.g., sodium lauryl sulphate). If desired, the tablets may be coated using suitable methods and coating materials such as OPADRY™ film coating systems available from Colorcon, West Point, PA (e.g., OPADRY™ OY Type, OYC Type, Organic Enteric OY-P Type, Aqueous Enteric OY-A Type, OY-PM Type and OPADRY™ White, 32K18400). Liquid preparation for oral administration may be in the form of solutions, syrups or suspensions. The liquid preparations may be prepared by conventional means with pharmaceutically acceptable additives such as suspending agents (e.g., sorbitol syrup, methyl cellulose or hydrogenated edible fats); emulsifying agent (e.g., lecithin or acacia); non-aqueous vehicles (e.g., almond oil, oily esters or ethyl alcohol); and preservatives (e.g., methyl or propyl p-hydroxy benzoates or sorbic acid).

The present disclosure also includes a multi-layer tablet comprising a layer providing for the delayed release of one or more compounds of the disclosure, and a further layer providing for the immediate release of another medication. Using a wax/pH-sensitive polymer mix, a gastric insoluble composition may be obtained in which the active ingredient is entrapped, ensuring its delayed release.

Parenteral Administration

For parenteral administration, the compounds of the disclosure may be formulated for injection or infusion, for example, intravenous, intramuscular or subcutaneous injection or infusion, or for administration in a bolus dose and/or continuous infusion. Suspensions, solutions or emulsions in an oily or aqueous vehicle, optionally containing other formulatory agents such as suspending, stabilizing and/or dispersing agents may be used.

Additional Administration Forms

Additional dosage forms of this disclosure include dosage forms as described in U.S. Pat. Nos. 6,340,475; 6,488,962; 6,451,808; 5,972,389; 5,582,837; and 5,007,790. Additional dosage forms of this disclosure also include dosage forms as described in U.S. Patent Applications Nos. 20030147952; 20030104062; 20030104053; 20030044466; 20030039688; and 20020051820. Additional dosage forms of this disclosure also include dosage forms as described in PCT Applications Nos. WO 03/35041; WO 03/35040; WO 03/35029; WO 03/35177; WO 03/35039; WO 02/96404; WO 02/32416; WO 01/97783; WO 01/56544; WO 01/32217; WO 98/55107; WO 98/11879; WO 97/47285; WO 93/18755; and WO 90/11757.

Controlled Release Formulations and Drug Delivery Systems

In certain embodiments, the formulations of the present disclosure may be, but are not limited to, short-term, rapid-offset, as well as controlled, for example, sustained release, delayed release and pulsatile release formulations.

The term sustained release is used in its conventional sense to refer to a drug formulation that provides for gradual release of a drug over an extended period of time, and that may, although not necessarily, result in substantially constant blood levels of a drug over an extended time period. The period of time may be as long as a month or more and should be a release which is longer that the same amount of agent administered in bolus form.

For sustained release, the compounds may be formulated with a suitable polymer or hydrophobic material which provides sustained release properties to the compounds. As such, the compounds for use the method of the disclosure may be administered in the form of microparticles, for example, by injection or in the form of wafers or discs by implantation.

In certain embodiments of the disclosure, the compounds of the disclosure are administered to a patient, alone or in combination with another pharmaceutical agent, using a sustained release formulation.

The term delayed release is used herein in its conventional sense to refer to a drug formulation that provides for an initial release of the drug after some delay following drug administration and that mat, although not necessarily, includes a delay of from about 10 minutes up to about 12 hours.

The term pulsatile release is used herein in its conventional sense to refer to a drug formulation that provides release of the drug in such a way as to produce pulsed plasma profiles of the drug after drug administration.

The term immediate release is used in its conventional sense to refer to a drug formulation that provides for release of the drug immediately after drug administration.

As used herein, short-term refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes and any or all whole or partial increments thereof after drug administration after drug administration.

As used herein, rapid-offset refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes, and any and all whole or partial increments thereof after drug administration.

Dosing

The therapeutically effective amount or dose of a compound of the present disclosure depends on the age, sex and weight of the patient, the current medical condition of the patient and the progression of Sigma-receptor related disorders or diseases in the patient being treated. The skilled artisan is able to determine appropriate dosages depending on these and other factors.

A suitable dose of a compound of the present disclosure may be in the range of from about 0.01 mg to about 5,000 mg per day, such as from about 0.1 mg to about 1,000 mg, for example, from about 1 mg to about 500 mg, such as about 5 mg to about 250 mg per day. The dose may be administered in a single dosage or in multiple dosages, for example from 1 to 4 or more times per day. When multiple dosages are used, the amount of each dosage may be the same or different. For example, a dose of 1 mg per day may be administered as two 0.5 mg doses, with about a 12-hour interval between doses.

It is understood that the amount of compound dosed per day may be administered, in non-limiting examples, every day, every other day, every 2 days, every 3 days, every 4 days, or every 5 days. For example, with every other day administration, a 5 mg per day dose may be initiated on Monday with a first subsequent 5 mg per day dose administered on Wednesday, a second subsequent 5 mg per day dose administered on Friday, and so on.

In the case wherein the patient's status does improve, upon the doctor's discretion the administration of the modulator of the disclosure is optionally given continuously; alternatively, the dose of drug being administered is temporarily reduced or temporarily suspended for a certain length of time (i.e., a "drug holiday"). The length of the drug holiday optionally varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday includes from 10%-100%, including, by way of example only, 10%, 15%,20%,25%,30%, 35%, 40%, 45%, 50%, 55%, 60%, 65%, 70%, 75%, 80%, 85%, 90%, 95%, or 100%.

Once improvement of the patient's conditions has occurred, a maintenance dose is administered if necessary. Subsequently, the dosage or the frequency of administration, or both, is reduced, as a function of the viral load, to a level at which the improved disease is retained. In certain embodiments, patients require intermittent treatment on a long-term basis upon any recurrence of symptoms and/or infection.

The compounds for use in the method of the disclosure may be formulated in unit dosage form. The term "unit dosage form" refers to physically discrete units suitable as unitary dosage for patients undergoing treatment, with each unit containing a predetermined quantity of active material calculated to produce the desired therapeutic effect, optionally in association with a suitable pharmaceutical carrier. The unit dosage form may be for a single daily dose or one of multiple daily doses (e.g., about 1 to 4 or more times per day). When multiple daily doses are used, the unit dosage form may be the same or different for each dose.

Toxicity and therapeutic efficacy of such therapeutic regimens are optionally determined in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index, which is expressed as the ratio between $LD_{50}$ and $ED_{50}$. Capsid assembly modulators exhibiting high therapeutic indices are preferred. The data obtained from cell culture assays and animal studies are optionally used in formulating a range of dosage for use in human. The dosage of such capsid assembly modulators lies preferably within a range of circulating concentrations that include the $ED_{50}$ with minimal toxicity. The dosage optionally varies within this range depending upon the dosage form employed and the route of administration utilized.

Those skilled in the art recognizes, or is able to ascertain using no more than routine experimentation, numerous equivalents to the specific procedures, embodiments, claims, and examples described herein. Such equivalents were considered to be within the scope of this disclosure and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present disclosure. Moreover, all values that fall within these ranges, as well as the upper or lower limits of a range of values, are also contemplated by the present application.

The examples described herein illustrate aspects of the present disclosure. However, they are in no way a limitation of the teachings or disclosure of the present disclosure as set forth herein.

The examples described herein are provided for purposes of illustration only, and are not intended to be limiting unless otherwise specified. Thus, the disclosure should in no way be construed as being limited to the examples described herein, but rather, should be construed to encompass any and all variations which become evident as a result of the teaching provided herein.

Without further description, it is believed that one of ordinary skill in the art can, using the description and illustrative examples, make and utilize the compounds of the present disclosure and practice the claimed methods. The working examples therefore, specifically point out selected embodiments of the present disclosure, and are not to be construed as limiting in any way the remainder of the disclosure.

The disclosures of each and every patent, patent application, and publication cited herein are hereby incorporated herein by reference in their entirety.

While this disclosure has been disclosed with reference to specific embodiments, it is apparent that other embodiments and variations of this disclosure may be devised by others skilled in the art without departing from the true spirit and scope of the disclosure. The appended claims are intended to be construed to include all such embodiments and equivalent variations.

EXAMPLES

The disclosure is now described with reference to the following Examples. These Examples are provided for the purpose of illustration only, and the disclosure is not limited to these Examples, but rather encompasses all variations that are evident as a result of the teachings provided herein.

Example 1

Coronaviruses (CoV) replicate in the cytoplasm of host cells and in the process co-opt cellular membranes and machinery to produce and assemble new infectious viral particles for dissemination throughout the infected organism. Initiation of CoV replication is completely dependent on the ER. Conversely, the CoV life cycle and associated activities have a profound impact on ER function. Viral replication rapidly produces substantial amounts of viral proteins that are co- or post-translationally inserted into the ER and targeted to the site of particle assembly, largely in the ER-Golgi intermediate compartment (ERGIC). Assembled viral particles in the ERGIC are transported to the cell surface via the secretory pathway and infectious virions released from the host cell by exocytosis.

SARS-CoV-2 Spike (S) Protein.

The spike (S) protein that forms protrusions on the surface of mature virions gives coronaviruses their characteristic crown-like appearance when viewed by electron microscopy. The S protein mediates selective virus entry into host cells, is the primary determinant of tissue tropism and viral host range, and is a major trigger of host immune responses. Infection and cytopathic effects (CPE) do not occur in the absence of functional S protein. Many viruses, CoVs included, readily adapt to new environments through mutation and recombination of their S protein (or equivalent). This ability to adapt can broaden the host range to promote cross-species infection and is intrinsic to many viruses. Therefore, neutralizing antibodies tend to lose their efficacy because of changes in the S protein receptor binding domain. In the case of CoVs, sera from recovered SARS 2003 and COVID19 patients whose S proteins share significant homology show limited cross-neutralization. Additionally, a recently discovered mutation in the S protein was linked to increased virulence and proposed as a contributing factor to differences in virulence and mortality between SARS-CoV-2 viral clades on the West and East Coast of the U.S.

Receptor binding and membrane fusion are the initial and critical steps in CoV infection. The CoV S glycoprotein is a typical class I viral fusion protein that consists of two principal components: an ectodomain consisting of a receptor-binding subunit S1, a single-pass transmembrane domain containing a membrane-fusion subunit S2. During virus entry, S1 of SARS-CoV and CoV-2 binds to the host cell surface receptor angiotensin converting enzyme 2 (ACE2). ACE2 binding destabilizes the prefusion Spike resulting in shedding of the S1 subunit and S2 mediated fusion of the host and viral membranes, subsequently allowing viral genomes to enter host cells. Protease cleavage is required for activation of the fusion potential of S glycoprotein of SARS-CoV-2 S protein and related viruses, SARS-CoV and MERS-CoV. In the case of SARS-CoV and CoV-2, Spike is cleaved by transmembrane protease serine protease-2 (TMPRSS2) in lung epithelial cells.

Transmembrane Protease Serine Protease-2 (TMPRSS2).

SARS-CoV and -CoV-2 Spike are activated by TMPRSS2; enhanced TMPRSS2 expression promotes increased infectivity in both in vitro and in vivo mouse models of SARS-CoV lung infection. TMPRSS2 is an androgen-induced, androgen receptor (AR) target gene which is a putative contributing factor to the apparently increased virulence of COVID19 in men, although it remains unclear if this holds true in a broader population analysis. In addition to its role in the secretory pathway, Sigma1 regulates AR signaling and that Sigma1 modulators can block TMPRSS2 induction by androgens (FIGS. 1A-1D).

Figure 2A:
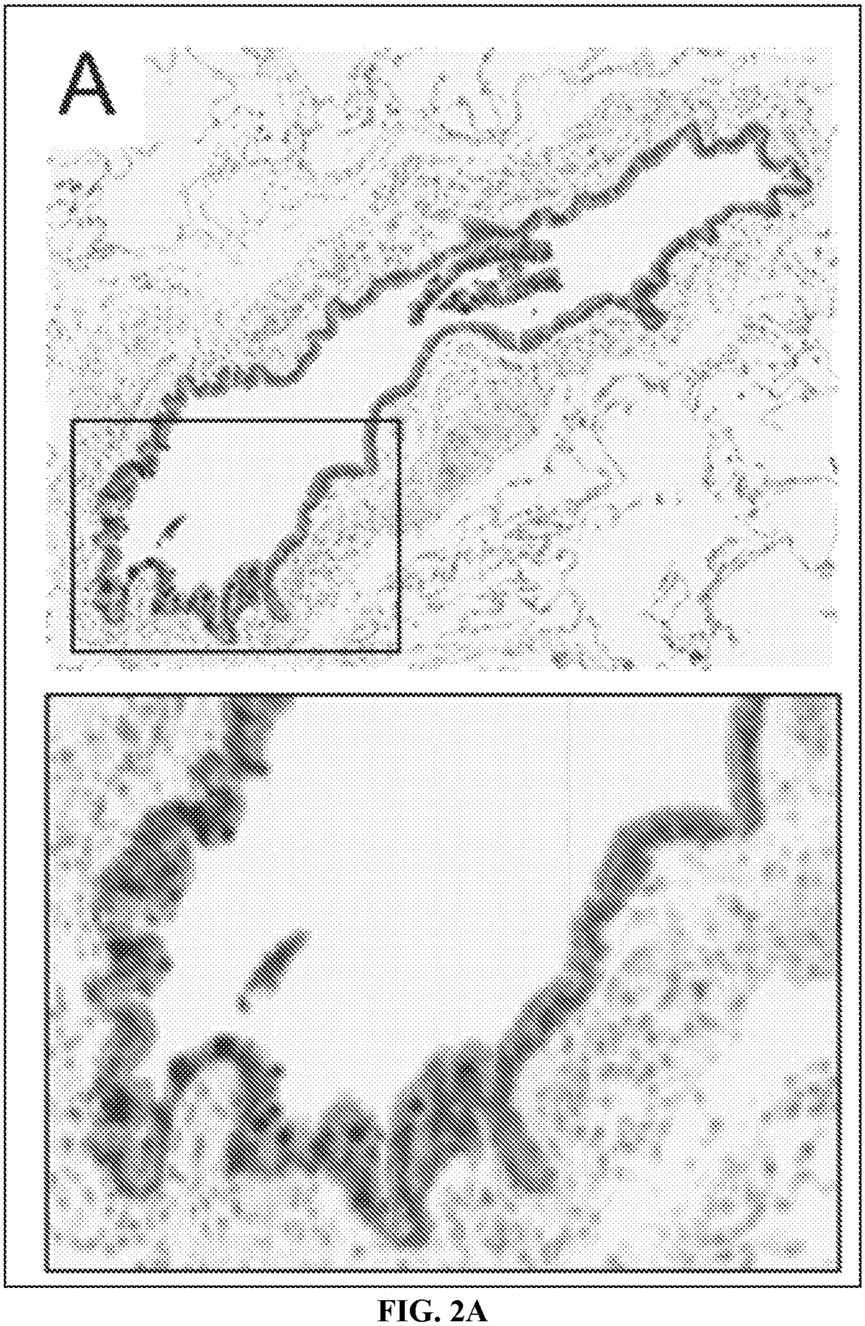
FIGS. 2A-2D illustrate the finding that Sigma1 is expressed in lungs and SIGMAR1 mRNA levels are enriched in alveolar type II (AT2) epithelial cells and correlate with ACE2 and TMPRSS2 transcript levels.
Figures 2B, 2C, 2D:
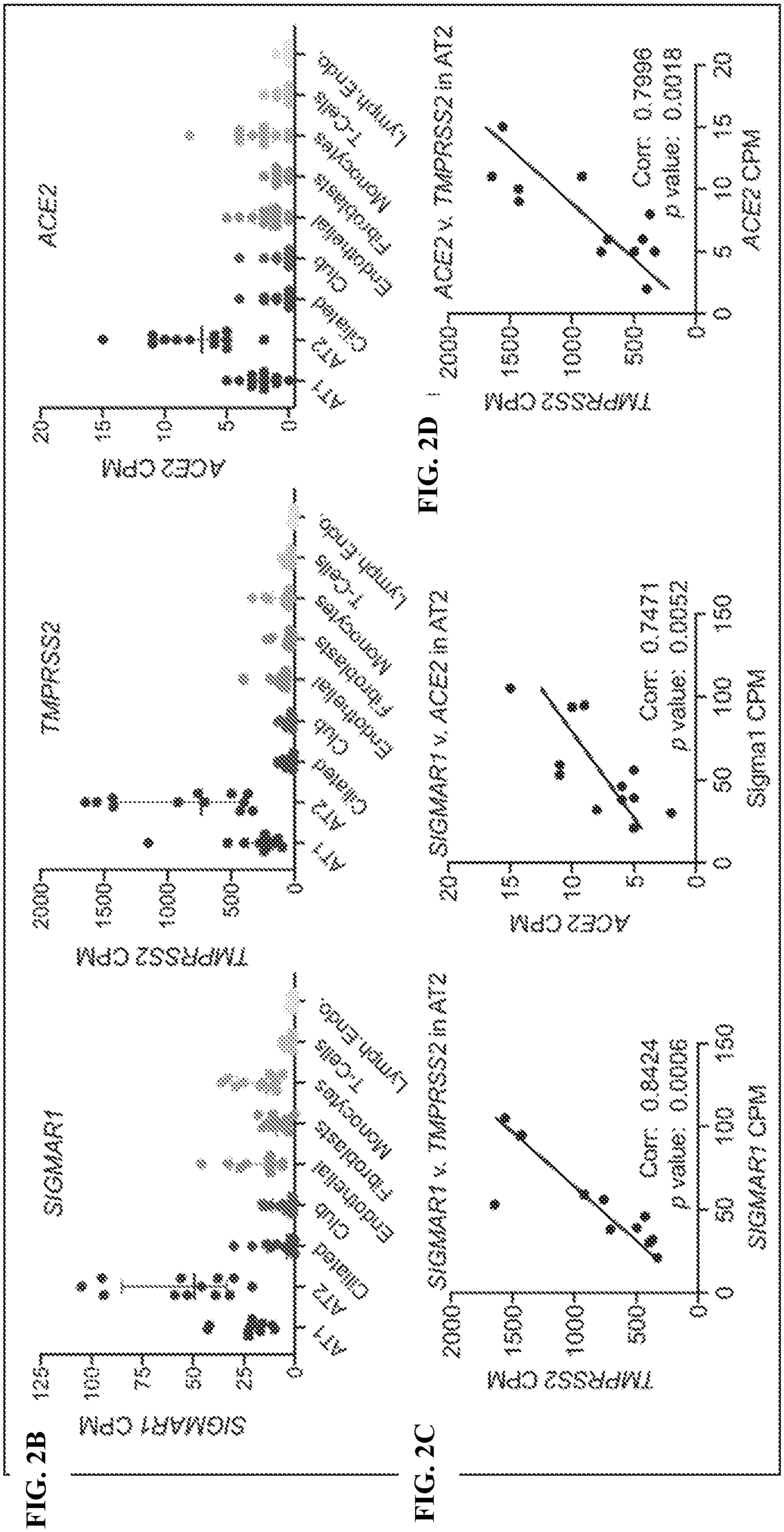

Example 2: Sigma1/SIGMAR1, TMPRSS2, and ACE2 Expression in Lung Alveolar Type II (AT2) Epithelial Ccells SIGMAR1/Sigma1 is abundantly expressed in the lung (FIGS. 2A-2B). Although a role for SIGMAR1/Sigma1 in lung physiology and pathophysiology has not been clearly established, Sigma1 may play a role in lung inflammation and stress leading to fibrosis. A consequence of the secretory pathway regulating properties of Sigma1 modulators is that they can also be used to elicit immune modulatory and anti-inflammatory effects. Particularly high expression of ACE2 and TMPRSS2 transcripts were observed specifically in lung alveolar type II (AT2) cells with a significant correlation between transcripts of the two genes (FIGS. 2B & 2D). Analysis of the dataset showed that SIGMAR1 is also highly enriched in AT2 cells and has a highly significant correlation with TMPRSS2 and ACE2 expression (FIGS. 2B-2C).

Example 3: Identification of Small Molecule Sigma1 Modulators That Suppress Infectivity of Replication Competent SARS-CoV-2

In certain embodiments, compounds that bind Sigma1 and trigger ER stress can block SARS-CoV-2 replication, as measured by quantitative qRT-PCR assay of viral infection and replication and associated cytopathic effects (CPE) assessed by an in vitro plaque assay.

Figure 3:
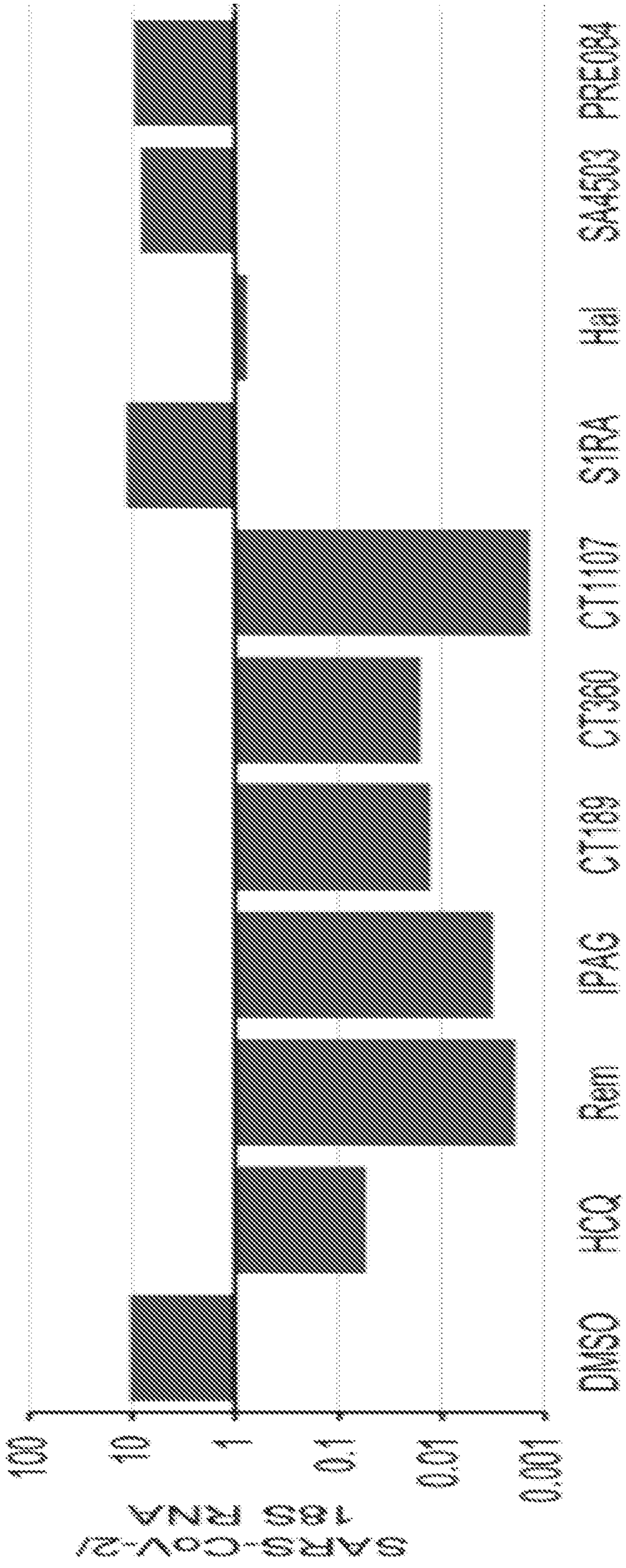
FIG. 3 illustrates the finding that only certain Sigma1 inhibitors block SARS-CoV-2 infection. Infection of Huh7.5 cells by replication competent SARS-CoV-2 in the presence of 10 μM Sigma1 Inhibitor/antagonist—IPAG (also known as 1-(4-iodophenyl)-3-(2-adamantyl)guanidine), CT189 (also known as 1-(4-chlorophenyl)-3-(3-(4-fluorophenoxy)-prop-1-yl)guanidine), CT360 (also known as methyl 6-(3-(2,2-dimethyl-3-(4-(trifluoromethyl)phenoxy)propyl)guanidino)nicotinate), CT1107 (also known as 1-(5-cyano-4-methoxypyridin-2-yl)-3-(3-methyl-3-(4-(trifluoromethyl) phenyl)butyl)guanidine), S1RA (also known as 4-[2-[[5-methyl-1-(2-naphthalenyl)-1H-pyrazol-3-yl]oxy]ethyl] morpholine), haloperidol (also known as 4-[4-(4-chlorophenyl)-4-hydroxypiperidin-1-yl]-1-(4-fluorophenyl) butan-1-one; or Hal)—or 10 μM Sigma1 Activator/agonist: SA4503 (also known as 1-(3,4-dimethoxyphenethyl)-4-(3-phenylpropyl) piperazine), PRE084 (also known as 2-morpholin-4-ylethyl 1-phenylcyclohexane-1-carboxylate). Results can be compared to vehicle (DMSO), Remdesivir (Rem, 10 μM), and hydroxychloroquine (HCQ, 10 μM). Compounds and SARS-CoV-2 were added to cell culture; 24 hours post inoculation relative infection calculated by qRT-PCR.

A discrete set of Sigma1 modulators was tested in an assay of replication competent SARS-CoV-2 infectivity. Only Sigma1 inhibitors that induce ER stress (i.e., CT1107, IPAG, CT189, and haloperidol) suppressed SARS-CoV-2 infection, in rank order of ER stress inducing potency. Strikingly, IPAG, CT189, and CT1107 blocked SARS-CoV-2 infection by 1,000 (IPAG, CT189, CT360) to 10,000 (CT1107) fold. Haloperidol had a clear but modest antiviral effect. In contrast, Sigma1 activators (SA4503 and PRE084), which not induce ER stress, did not block infection. S1RA, a putative antagonist that does not induce ER stress, did not block infection (FIG. 3).

A pharmacophore and hypothesis driven screen of Sigma1 modulator compounds is performed in an in vitro infectivity assay using replication competent SARS-CoV-2 virus. Changes in the status of SIGMAR1 transcript and Sigma1 protein in infected cells are monitored to probe the role of Sigma1 in the infected host cell and in viral replication.

Infection Assays.

Infectivity assays are performed using replication competent SARS-CoV-2 virus. Compounds with diverse Sigma1 pharmacology (including those tested in Huh7.5 cell lines in FIG. 3) that bind Sigma1 but induce distinct molecular actions are screened. Traditional plaque/cytopathic effect (CPE) assays are performed using replication competent infectious SARS-CoV-2 virus to identify compounds that block infection with an anti-viral $TCID_{50}$ of <10 μM. Standard CoV induced plaque assays and qRTPCR based viral titer calculations are performed. VeroE6 (ATCC CRL-1586), and VeroE6/TMPRSS2 (stably transfected to express high levels of TMPRSS2) are used to model differences in response by susceptible and highly susceptible cells to CoV-2 infection, replication, and CPE. VeroE6 cells are a widely used, standard model cell line for CoV studies and express high levels of angiotensin converting enzyme 2 (ACE2), the cognate receptor for SARS-CoV and SARS-CoV-2.

Sigma1 Inhibitor is Antiviral in Multiple Cell Types.

Figure 8:
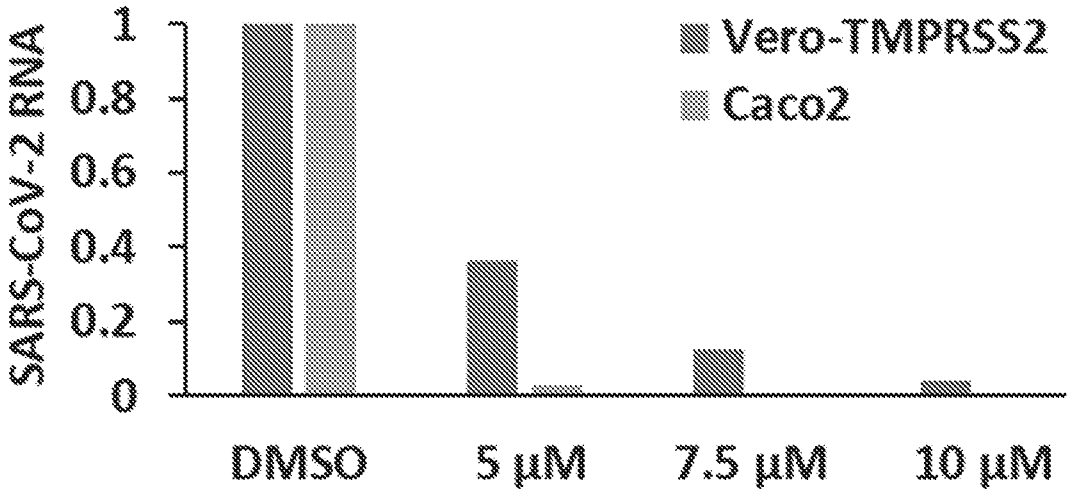
FIG. 8 illustrates results obtained when VeroE6/TMPRSS2 or Caco2 cells were treated with DMSO or 5 μM, 7.5 μM, and 10 μM CT1107 and infected with SARS-CoV-2 for 48 hours. RNA was isolated and qRT-PCR was performed with virus-specific and 18S primers. Viral RNA was normalized to 18S RNA.

It was tested whether Sigma1-targeting compounds are antiviral in additional cell lines. VeroE6 cells stably expressing TMPRSS2and Caco-2 (human colorectal epithelial cells) were tested. As shown in FIG. 8, compound CT1107 was potently antiviral in these cell types, without toxicity. In certain embodiments, these compounds are antiviral in primary respiratory epithelial cells.

SIGMAR1/Sigma1 Status in CoV Infected Cells.

In certain embodiments, if Sigma1 is acutely engaged and utilized during viral replication, biomarkers of Sigma1 involvement in viral replication might include upregulation of SIGMAR1 mRNA transcripts and Sigma1 protein as well as altered subcellular distribution of Sigma1 to reflect engagement by viral proteins. To evaluate these potential biomarkers, SIGMAR1 mRNA transcript levels are monitored by qRT-PCR, and Sigma1 protein levels and distribution patterns are monitored by IB and immunocytochemical (ICC) staining in replication competent CoV-2 infected cells in vitro. Differences in levels and/or localization of Sigma1 may reflect differential protein-interactions, which can be evaluated with protein-pulldown and proximity ligation assays to determine likely changes in Sigma1 associated protein complexes relevant to viral replication.

Example 4: Characterization of Impact of Sigma1 Modulators on SARS-CoV-2 Spike (S) Protein and Host Cell TMPRSS2

In certain embodiments, Sigma1 targeting agents that trigger prolonged ER stress can block the maturation of and eliminate the SARS-CoV-2 S protein and/or decrease TMPRSS2 levels to suppress viral infection. Key mechanisms by which efficacious antiviral Sigma1 modulators block SARS-CoV-2 viral entry can be identified and characterized. SARS-CoV-2 Spike is activated by TMPRSS2 whose enhanced expression promotes infectivity in vitro and in vivo. As Spike and TMPRSS2 are integral membrane glycoproteins with multiple N-glycosylation sites, they are both dependent on the ER for translation and post-translational modification (PTM) for maturation and transport to the cell surface.

The functional impact of Sigma1 modulators on S protein induced cell-to-cell fusion is evaluated when expressed independently in Vero E6 cells. Changes in S protein incorporation into pseudovirions, and thus the impact of Sigma1 modulators on production of infectious viral particle, are also evaluated. For S protein studies, the following plasmid constructs can be used: untagged parental SARS-CoV-2 S protein; 3xFLAG tagged S protein described by Ou et al., 2020, Nature communications 11:1620; HA-tagged S protein described by Hoffman et al., 2020, Cell, doi:10.1016/j.cell.2020.02.052. TMRPSS2 focused assays can be used to determine levels and localization of protein, cell-to-cell fusion efficiency and infectivity of Sigma1 modulator treated VeroE6 and VeroE6/TMRPSS2 host cells.

Western Blot Data Support Antiviral Mechanism of Action of Specific Sigma1-Targeting Compounds.

Figure 4:
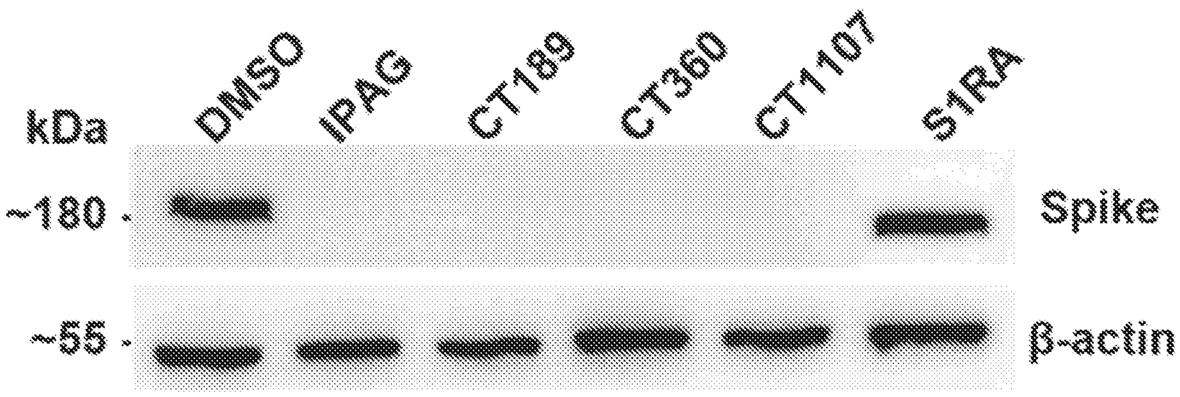
FIG. 4 illustrates results obtained when Huh7.5 cells were treated with compounds at 10 μM for 2 h, then infected with SARS-CoV-2 for 24 h. Lysates were probed with α-spike and α-β actin antibodies. Western blot is representative of two experimental replicates.

Only certain Sigma1 inhibitors, those that induce ER stress and autophagy (IPAG, CT189, CT360, CT1107), inhibit SARS-CoV-2 infection, while a putative Sigma1 antagonist that does not induce ER stress or autophagy (S1RA) does not block infection (FIG. 1). As shown in FIG. 4, treatment of human Huh7.5 cells with these Sigma1 selective inhibitors resulted in a striking decrease in SARS-CoV-2 Spike protein 48 hours post-infection, while treatment with S1RA (which binds Sigma1 with high affinity but does not trigger ER stress and autophagy) did not. Importantly toxicity in these cells was not observed at the concentrations tested.

Impact of Sigma1 Modulation on Spike and TMPRSS2 Mediated Cell-to-Cell Fusion.

This assay is a direct measure of S protein-receptor binding and fusogenic activity. Cell surface expression of S protein, independent of other viral proteins, can trigger the fusion of cells expressing S protein at their surface with cells expressing its cognate receptor, ACE2. Subsequent to binding its receptor ACE2, S protein's fusogenic activity is triggered by co-expressed TMPRSS2-mediated cleavage on the surface of the host cell. In this assay, expression of S protein triggered cell-to-cell fusion can induce the formation of multinucleated cellular syncytia, the readout of common cell fusion assays. Evaluating TMPRSS2 is important here because the SARS-CoV and -CoV-2 S proteins are proteolytically activated by TMPRSS2 and saliently increases SARS-CoV and SARS-CoV-2 replication and syncytium formation in vitro and in vivo.

This assay can be performed using VeroE6 cells and VeroE6/TMPRSS2 cells which over express TMPRSS2 and that are highly susceptible to SARS-CoV-2 infection and promote virus-host cell membrane fusion independent of endocytosis. This assay essentially can be performed as described elsewhere (Hoffmann, et al., 2020, Cell, doi: 10.1016/j.cell.2020.02.052) with minor modifications. A beta-galactosidase reporter plasmid was transfected into the VeroE6 cells previously published to detect single fusion events as well as larger syncytia (Kim, et al., 2003, J. Virol. 77:963-969). Sigma1 shRNA knockdown studies are also conducted in these cells to confirm that Sigma1 is required for expression, maturation, localization, and fusogenic activity of S protein. Cell-to-cell fusion of VeroE6 and VeroE6/TMPRSS2 cells treated with Sigma1 modulators and/or in which Sigma1 is knocked down with shRNA are compared.

Sigma1 Inhibitor Blocks the Formation of Syncytia in Cells Expressing SARS-CoV-2 Spike and TMPRSS2.

Figure 5:
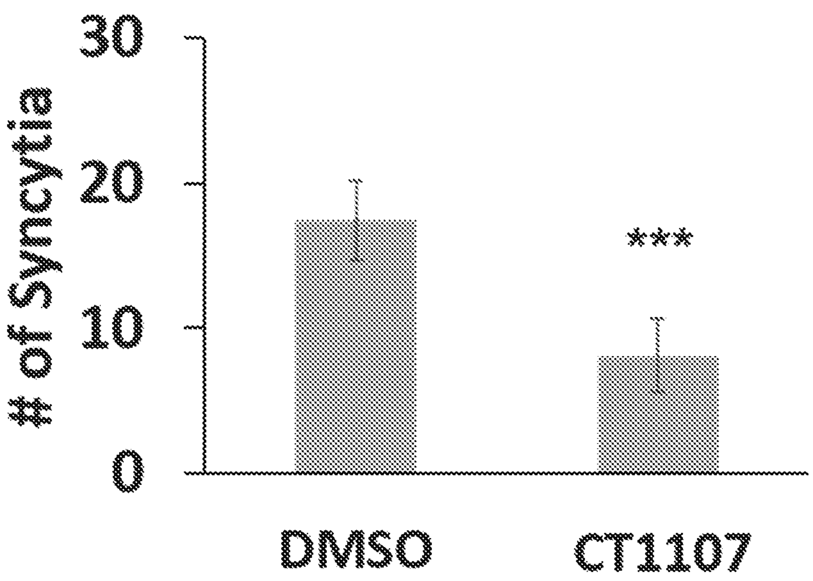
FIG. 5 illustrates results obtained when Vero E6 cells were transfected with plasmids expressing spike and TMPRSS2 and treated with DMSO or 10 μM CT1107. Cells were fixed and stained with Giemsa and syncytia were counted. Shown is the average of four experimental replicates, with five fields counted per replicate. ***p<0.0005.
Figure 6:
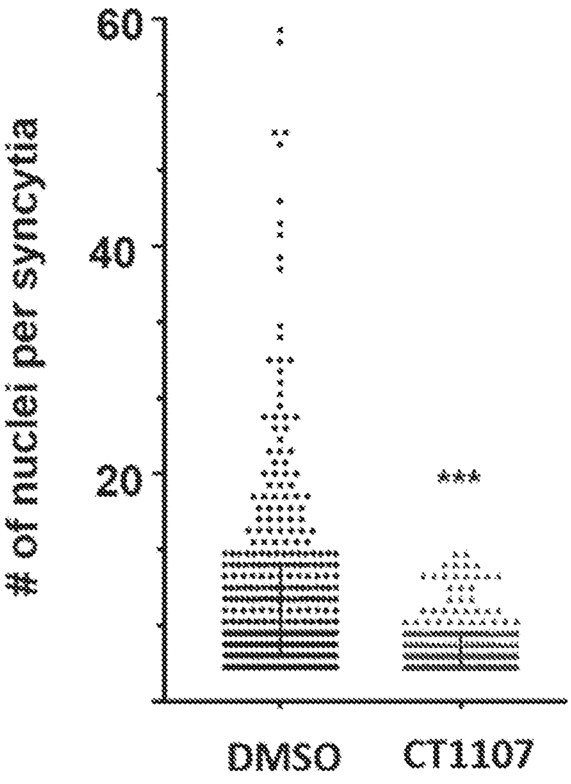
FIG. 6 illustrates observed number of nuclei per syncytia when experiments were done as in FIG. 5. Data from four replicates, with number of nuclei per syncytia in five fields counted per replicate. ***p<0.0005.
Figure 7:
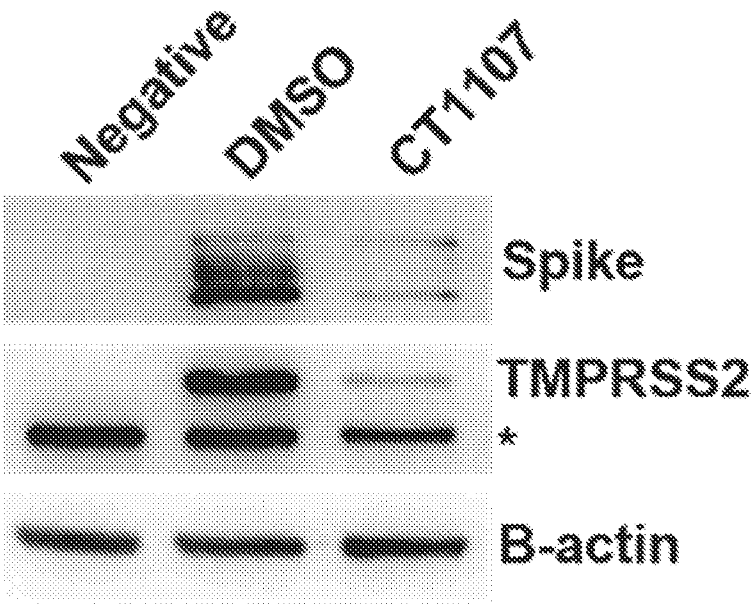
FIG. 7 illustrates results obtained when Vero E6 cells were transfected with plasmids expressing spike and TMPRSS2 and treated with DMSO or 10 μM CT1107. Lysates were harvested and probed with α-spike, α-TMPRSS2 or α-β actin antibodies. (*-non-specific band). Western blot is representative of four replicates.

SARS-CoV-2 infected cells fuse with neighboring cells to form syncytia, mediated by the viral spike protein interacting with the cellular ACE2 receptor and enhanced by the host cellular protease, TMPRSS2. VeroE6 cells were transfected with plasmids expressing SARS-CoV-2 spike and human TMPRSS2 and the number of syncytia formed (indicator of frequency of cell-cell fusion events) and the number of nuclei per syncytia (indicator of magnitude of Spike triggered cell fusion and potential cytopathic effect) were measured in DMSO and CT1107 treated cells (FIGS. 5-6). CT1107 was selected because it was the most potent inhibitor of CoV-2 infection in our initial experiments (FIGS. 1A-1D). The data show a significant decrease in both the number (FIG. 5) and the size of syncytia (FIG. 6) in CT1107-treated cells, compared to controls. In certain non-limiting embodiments, certain Sigma1 inhibitors can inhibit infection by targeting the CoV-2 Spike protein and host cell TMPRSS2 for degradation. Protein lysates from the cells in the syncytia assays were immunoblotted for Spike and TMPRSS2. In FIG. 7, a clear decrease in both Spike and TMPRSS2 protein is observed in CT1107-treated cells.

Spike and TMPRSS2 Protein Levels, Localization, and Post-Translational Modification.

In certain embodiments, Sigma1 modulators can selectively trigger proteasomal and autolysosomal degradation of membrane associated and integral membrane proteins. Changes in total cellular S protein levels can be evaluated by immunoblot. Changes in S protein glycosylation are evaluated by performing EndoH and PNGase F sensitivity assays. Sigma1 modulator induced changes to S protein cell surface expression can be evaluated by surface biotinylation/pull-down assay and orthogonally by confocal microscopy. Using VeroE6 and VeroE6/TMRPSS2 cells, it can be tested whether Sigma1 modulators decrease TMPRSS2 protein levels by proteasomal or autolysosomal degradation and if their maturation is blocked by disruption of N-glycosylation in ER.

Incorporation of SARS-CoV-2 S Protein into Pseudotyped Viral Particles.

This assay can test impact of Sigma1 modulators on S glycoprotein maturation and incorporation into pseudovirions. Pseudovirions can be produced using a lentiviral vector and packaging system with SARS-CoV-2 S glycoprotein. Pseudovirions can be produced by co-transfecting 293T cells with psPAX2, pLenti-CMVGFP/Luc, and SARS-CoV-2 S plasmids. The efficiency of SARS-CoV-2 S protein incorporation into lentiviral pseudovirions canl be evaluated by immunoblot of isolated viral particles from the cell culture medium.

Example 5: Determining Whether Sigma1 Modulators Restrict SARS-CoV-2 Infection in Primary Cells and a Syrian Golden Hamster Model of Infection Sigma1 modulators can inhibit SARS-CoV-2 infection in vitro using cell line models. A repertoire of primary lung cells are tested, and antiviral efficacy of Sigma1 modulators are evaluated, in vivo, in a Syrian hamster model of SARS-CoV-2 infection and pathology.

SIGMAR1 expression is elevated in AT2 cells and this correlates with the expression of ACE2 and TMPRSS2 (FIGS. 2A-2D). It is assessed whether Sigma1 modulators are antiviral in commercially-available primary airway cells, beginning with human AT2 cells (Accegen Biotech) and human iPSC-derived alveolar epithelial cells (Cell Applications). These studies are extended to primary nasal epithelial (Epithelix), bronchial epithelial (Lonza), human small airway epithelial (Lonza), and bronchial/tracheal epithelial cells (ATCC). Without wishing to be limited by any theory, it is important to test cells from different airways regions as CoV-2 can infect diverse tissue in people. These cells are cultured in air-liquid interface (ALI) cultures, which mimic the airway.

Syrian golden hamsters are a useful small animal model for both SARS-CoV and SARS-CoV-2 infection. CoV-2 replicates efficiently in the lungs of these animals and causes pathological lesions similar to those of COVID19 patients with pneumonia. Additionally, CoV-2 was transmitted from infected to naive hamsters via aerosols, providing further support that this model is similar to human infection. Sigma1 modulators are tested in this model of infection to further evaluate the possibility of using these molecules as therapeutic agents in SARS-CoV-2 infection and pathology.

Infections of Syrian Golden Hamsters with SARS-CoV-2.

Figure 9:
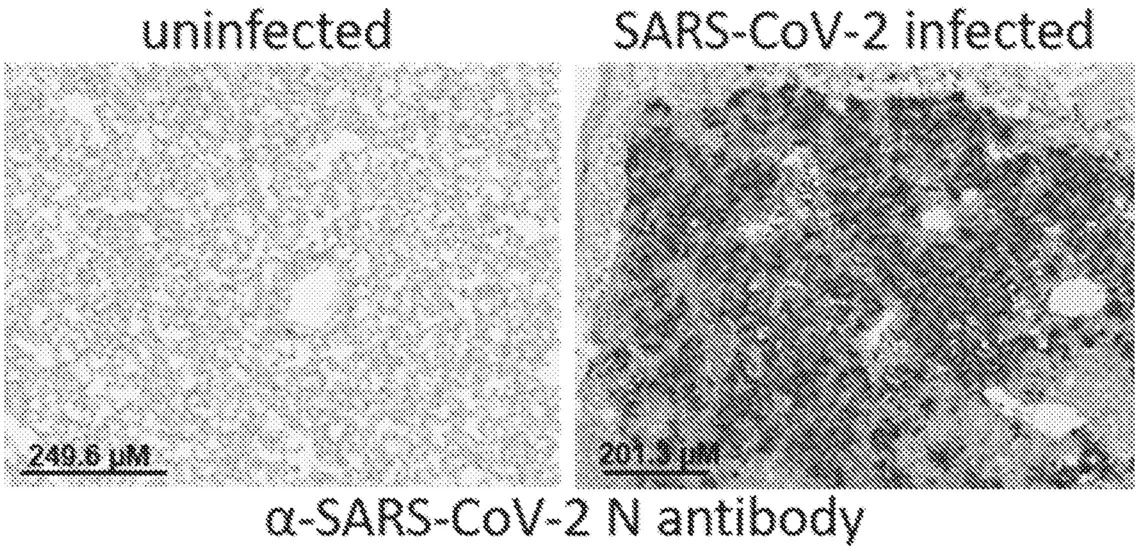
FIG. 9 illustrates the finding that SARS-CoV-2 nucleocapsid protein is detected in Syrian golden hamster lungs at 3 days p.i. but is absent in uninfected hamsters.

Syrian golden hamsters can be with Sigma1-targeting agents to determine whether these compounds are antiviral in vivo. The Syrian golden hamster model for SARS-CoV-2 infection was successfully established. FIG. 9 illustrates robust detection of SARS-CoV-2 nucleocapsid protein in the lungs of Syrian golden hamsters at 3 days post-infection, which is not present in uninfected controls. These data demonstrate that this model can be used to test the activity of Sigma1-targeting compounds in vivo.

Antiviral Activity of Sigma1 Modulators in Primary Airway Cells.

Cells are treated with compounds of interest at a concentration of 10 μM for 2 hours, followed by infection with SARS-CoV-2 at an MOI of 1. After 24, 48 and 72 hours, the media is aspirated, cells are collected in Trizol, RNA is extracted, and infection is measured by qRT-PCR using primers specific to the SARS-CoV-2 genome. For any compound that has antiviral activity, dose-response assays are perform to determine the $IC_{50}$ and $CC_{50}$ in these cultures. In addition to assessing infection by qPCR, viruses released from the apical side of the ALI cultures are also collected and viral titers assessed by $TCID_{50}$ assays. An important critical factor in evaluating the value of Sigma1 modulators as therapeutic agents for SARS-CoV-2 infection is to determine their effectiveness relative to the timing of viral infection, as these can be administered subsequent to infection. Therefore, it is evaluated whether the addition of Sigma1 modulators after viral infection in primary human cells is effective. Primary cells are infected with SARS-CoV-2 at an MOI of 1 and cells treated with Sigma1 modulators at 6, 12, and 24 h hour post-infection; viral infection is assessed by qRT-PCR. For all experiments, the expression of SIGMAR1, TMPRSS2, and ACE2 mRNA is monitored using qRT-PCR. Also monitored are the protein expression and localization of Sigma1, TMPRSS2 and ACE2 via immunoblotting and immunocytochemistry (ICC), respectively.

Ability of Sigma1 Modulators to Restrict SARS-CoV-2 Replication in a Hamster Model of Infection.

To determine if Sigma1 modulators are antiviral in a Syrian golden hamster model of infection, hamsters are treated with compounds that restrict CoV-2 infection in primary cells. The animals are administered 10 and 30 mg/kg of each compound or drug vehicle by i.p. injection the day before viral infection. Ten hamsters are used per group, with an equal number of males and females. All animals are implanted with microchips to allow to monitor body temperature over the course of the experiment (UID Identification Solutions). Hamsters are infected with CoV-2 ($TCID_{50}$ of $10^5$), delivered intranasally. At days 2, 4, and 8 after the infection, animals are euthanized, and nasal turbinates, lungs, livers, spleen, and kidneys are isolated. Nasal turbinates and one lung are used for extraction of the challenge virus for subsequent virus titration and virus quantification by qRT-PCR, as well as for quantitation of SIGMAR1 and TMPRSS2. Remaining lung is used for histological characterization of disease and for IHC staining of CoV-2 antigens. For the other organs, viral loads are determined by qRT-PCR to analyze the spread of the virus. To test whether Sigma1 modulators are antiviral when administered after infection, these experiments are performed as described elsewhere herein, with the exception that the compounds are administered at days 2 and 4 after infection, with euthanasia at 6 and 8 days. In certain embodiments, by combining biochemical MOA assays with in vitro and in vivo antiviral efficacy assays (infectivity and CPE), one can identify antiviral Sigma1 targeting compounds that have therapeutic utility.

Example 6

Figure 10:
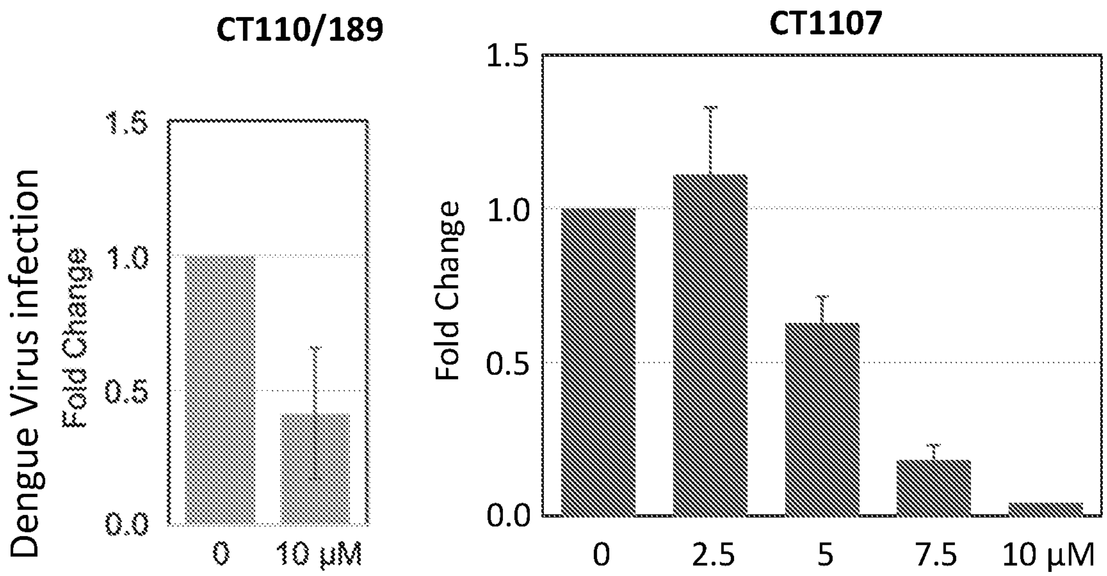
FIG. 10 illustrates the finding that compounds of the disclosure inhibit Dengue virus infection. U2OS cells were treated with DMSO or 10 μM of CT110 (also known as CT189, left graph) or DMSO or 2.5 μM, 5 μM, 7.5 μM, and 10 μM CT1107 (right graph). 2 hours after starting treatment, U2OS cells were infected with a multiplicity of infection (MOI) of 1 for Dengue Virus and incubated at 37° C. for ~16-18 hours. Cells were harvested with Trizol and RNA was extracted for qPCR. Y-axis indicates fold change in infection.

FIG. 10 illustrates the finding that compounds of the disclosure inhibit dengue virus infection. U2OS cells were treated with DMSO or 10 μM of CT110 (also known as CT189, left graph) or DMSO or 2.5 μM, 5 μM, 7.5 μM, and 10 μM CT1107 (right graph). 2 hours after starting treatment, U2OS cells were infected with a multiplicity of infection (MOI) of 1 for Dengue Virus and incubated at 37° C. for ~16-18 hours. Cells were harvested with Trizol and RNA was extracted for qPCR. Y-axis indicates fold change in infection.

Figure 11:
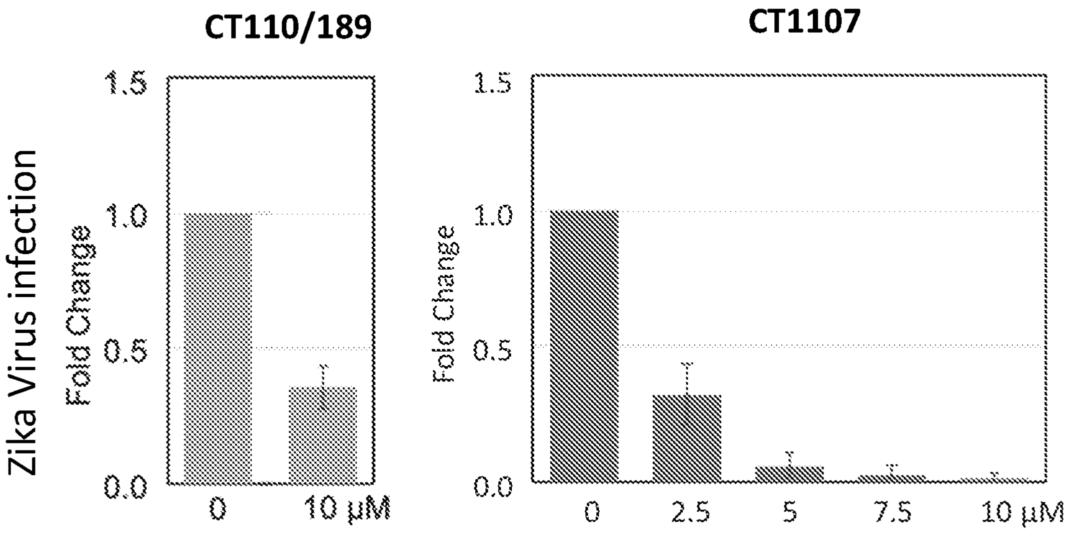
FIG. 11 illustrates the finding that compounds of the disclosure inhibit Zika virus infection. U2OS cells were treated with DMSO or 10 μM of CT110 (also known as CT189, left graph) or DMSO or 2.5 μM, 5 μM, 7.5 μM, and 10 μM CT1107 (right graph). 2 hours after starting treatment, U2OS cells were infected with a multiplicity of infection (MOI) of 1 for Zika Virus and incubated at 37° C. for ~16-18 hours. Cells were harvested with Trizol and RNA was extracted for qPCR. Y-axis indicates fold change in infection.

FIG. 11 illustrates the finding that compounds of the disclosure inhibit Zika virus infection. U2OS cells were treated with DMSO or 10 μM of CT110 (also known as CT189, left graph) or DMSO or 2.5 μM, 5 μM, 7.5 μM, and 10 μM CT1107 (right graph). 2 hours after starting treatment, U2OS cells were infected with a multiplicity of infection (MOI) of 1 for Zika Virus and incubated at 37° C. for ~16-18 hours. Cells were harvested with Trizol and RNA was extracted for qPCR. Y-axis indicates fold change in infection.

Figure 12:
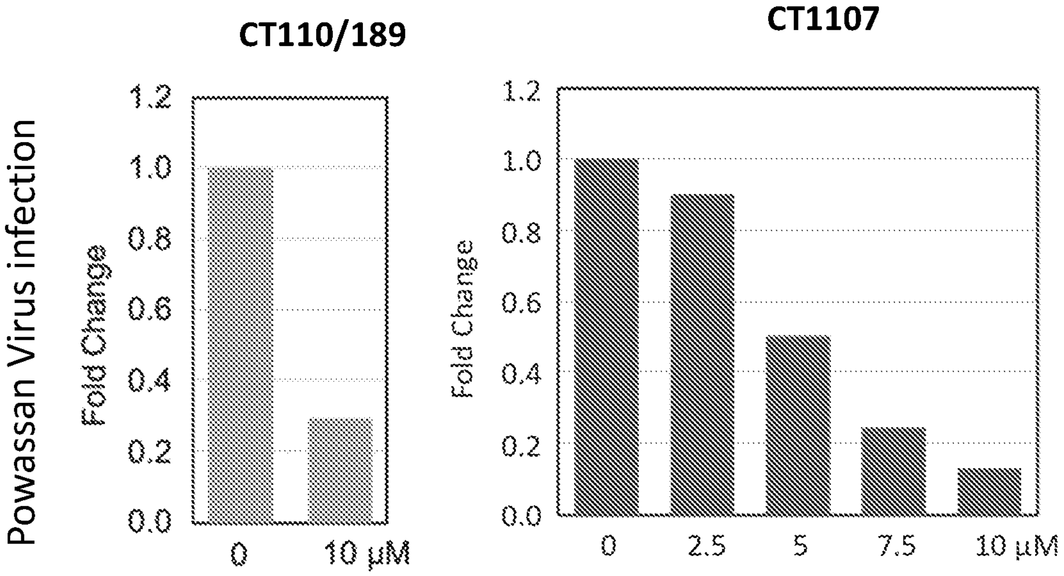
FIG. 12 illustrates the finding that compounds of the disclosure inhibit Powassan virus infection. U2OS cells were treated with DMSO or 10 μM of CT110 (also known as CT189, left graph) or DMSO or 2.5 μM, 5 μM, 7.5 μM, and 10 μM CT1107 (right graph). 2 hours after starting treatment, U2OS cells were infected with a multiplicity of infection (MOI) of 1 for Powassan Virus and incubated at 37° C. for ~16-18 hours. Cells were harvested with Trizol and RNA was extracted for qPCR. Y-axis indicates fold change in infection.

FIG. 12 illustrates the finding that compounds of the disclosure inhibit Powassan virus infection. U2OS cells were treated with DMSO or 10 μM of CT110 (also known as CT189, left graph) or DMSO or 2.5 μM, 5 μM, 7.5 μM, and 10 μM CT1107 (right graph). 2 hours after starting treatment, U2OS cells were infected with a multiplicity of infection (MOI) of 1 for Powassan Virus and incubated at 37° C. for ~16-18 hours. Cells were harvested with Trizol and RNA was extracted for qPCR. Y-axis indicates fold change in infection.

The disclosures of each and every patent, patent application, and publication cited herein are hereby incorporated herein by reference in their entirety. While this disclosure has been disclosed with reference to specific embodiments, it is apparent that other embodiments and variations of this disclosure may be devised by others skilled in the art without departing from the true spirit and scope of the disclosure. The appended claims are intended to be construed to include all such embodiments and equivalent variations.

What is claimed is:

1. A method of (a) disrupting virus lifecycle, infection, or dissemination in a virus-infected subject, or preventing or minimizing virus infection or dissemination in a subject, wherein the virus comprises at least one surface viral protein that is involved in viral entry or viral infection, (b) inhibiting, minimizing, or preventing formation of virus particles in a virus-infected subject, wherein the virus comprises at least one surface viral protein that is involved in viral entry or viral infection, (c) altering production, post-translational modification, assembly, maturation, or functional cell surface expression of at least one virus protein involved in viral entry or viral infection in a subject's cell, (d) initiating or stimulating selective autophagosomal, lysosomal, or proteasomal degradation of at least one virus protein involved in viral entry or viral infection in a subject's cell, (e) decreasing or inhibiting increase of amount, concentration, or production of at least one virus protein involved in viral entry or viral infection in a subject's cell, (f) altering or disturbing subcellular localization or virus promoting activity of at least one virus protein involved in viral entry or viral infection in a subject's cell, or (g) minimizing or preventing incorporation of a surface viral protein into a virion in a virus-infected eukaryotic cell, the method comprising administering to the subject a therapeutically effective amount of a compound of formula (I):

(I)

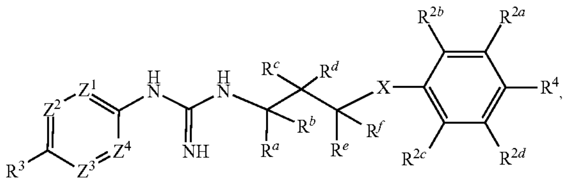

wherein:

one of the following applies:

| | | | |
|---|---|---|---|
| (a) $Z^1$ is $CR^{1a}$; | $Z^2$ is N; | $Z^3$ is $CR^{1c}$ or N; | $Z^4$ is $CR^{1d}$; |
| (b) $Z^1$ is N; | $Z^2$ is $CR^{1b}$; | $Z^3$ is $CR^{1c}$; | $Z^4$ is $CR^{1d}$ or N; |
| (c) $Z^1$ is $CR^{1a}$; | $Z^2$ is N; | $Z^3$ is $CR^{1c}$; | $Z^4$ is N; |
| (d) $Z^1$ is N; | $Z^2$ is $CR^{1b}$; | $Z^3$ is N; | $Z^4$ is $CR^{1d}$; |

X is selected from the group consisting of bond and O;

each occurrence of $R^{1a}$, $R^{1b}$, $R^{1c}$, and $R^{1d}$ is independently selected from the group consisting of hydrogen, $C_1$-$C_6$ alkyl, $C_1$-$C_6$ fluoroalkyl, $C_1$-$C_6$ heteroalkyl, F, Cl, Br, I, —CN, —$NO_2$, —$OR^5$, —$SR^5$, —S(=O)$R^5$, —S(=O)$_2R^5$, —NHS(=O)$_2R^5$, —C(=O)$R^5$, —OC(=O)$R^5$, —$CO_2R^5$, —$OCO_2R^5$, —CH$(R^5)_2$, —N$(R^5)_2$, —C(=O)N$(R^5)_2$, —OC(=O)N$(R^5)_2$, —NHC(=O)NH$(R^5)$, —NHC(=O)$R^5$, —NHC(=O)O$R^5$, —C(OH)$(R^5)_2$, and —C$(NH_2)(R^5)_2$;

each occurrence of $R^{2a}$, $R^{2b}$, $R^{2c}$, and $R^{2d}$ is independently selected from the group consisting of hydrogen, $C_1$-$C_6$ alkyl, $C_1$-$C_6$ fluoroalkyl, $C_1$-$C_6$ heteroalkyl, F, Cl, Br, I, —CN, —$NO_2$, —$OR^5$, —$SR^5$, —S(=O)$R^5$, —S(=O)$_2R^5$, —NHS(=O)$_2R^5$, —C(=O)$R^5$, —OC(=O)$R^5$, —$CO_2R^5$, —$OCO_2R^5$, —CH$(R^5)_2$, —N$(R^5)_2$, —C(=O)N$(R^5)_2$, —OC(=O)N$(R^5)_2$, —NHC(=O)NH$(R^5)$, —NHC(=O)$R^5$, —NHC(=O)O$R^5$, —C(OH)$(R^5)_2$, and —C$(NH_2)(R^5)_2$;

$R^3$ is selected from the group consisting of CN, F, Cl, Br, I, $C_1$-$C_6$ haloalkyl, $C_1$-$C_6$ haloalkoxy, and —C(O)O$R^6$;

$R^4$ is selected from the group consisting of CN, F, Cl, Br, I, $C_1$-$C_6$ haloalkyl, $C_1$-$C_6$ haloalkoxy, and —C(O)O$R^7$;

each occurrence of $R^5$ is independently selected from the group consisting of H, $C_1$-$C_6$ alkyl, $C_1$-$C_6$ heteroalkyl, aryl, and —$C_1$-$C_3$ alkyl-($C_3$-$C_6$ cycloalkyl), wherein the alkyl, heteroalkyl, aryl, or cycloalkyl group is optionally substituted;

$R^6$ is selected from the group consisting of H, $C_1$-$C_6$ alkyl, $C_1$-$C_6$ heteroalkyl, and $C_3$-$C_6$ cycloalkyl, wherein the alkyl, heteroalkyl, or cycloalkyl group is optionally substituted;

$R^7$ is selected from the group consisting of H, $C_1$-$C_6$ alkyl, $C_1$-$C_6$ heteroalkyl, and $C_3$-$C_6$ cycloalkyl, wherein the alkyl, heteroalkyl, or cycloalkyl group is optionally substituted; and each occurrence of $R^a$, $R^b$, $R^c$, $R^d$, $R^e$, and $R^f$ is independently selected from the group consisting of H and $CH_3$, with the proviso that, if $Z^3$ is $CR^{1c}$ and $Z^4$ is $CR^{1d}$, then at least one of $R^a$, $R^b$, $R^c$, $R^d$, $R^e$, and $R^f$ is $CH_3$, or a salt, solvate, enantiomer, diastereoisomer, tautomer, or N-oxide thereof.

2. The method of claim 1, wherein the virus comprises a flavivirus or a Coronavirus.

3. The method of claim 2, wherein the virus comprises the flavivirus, and wherein the flavivirus comprises at least one of at least one of Apoi virus, Aroa virus, Bamaga virus, Bagaza virus, Banzi virus, Bouboui virus, Bukalasa bat virus, Cacipacore virus, Carey Island virus, Cowbone Ridge virus, Dakar bat virus, Dengue virus, Edge Hill virus, Entebbe bat virus, Gadgets Gully virus, Ilheus virus, Israel turkey meningoencephalomyelitis virus, Japanese encephalitis virus, Jugra virus, Jutiapa virus, Kadam virus, Kedougou virus, Kokobera virus, Koutango virus, Kyasanur Forest disease virus, Langat virus, Louping ill virus, Meaban virus, Modoc virus, Montana myotis leukoencephalitis virus, Murray Valley encephalitis virus, Ntaya virus, Omsk hemorrhagic fever virus, Phnom Penh bat virus, Powassan virus, Rio Bravo virus, Royal Farm virus, Saboya virus, Saint Louis encephalitis virus, Sal Vieja virus, San Perlita virus, Saumarez Reef virus, Sepik virus, Tembusu virus, Tick-borne encephalitis virus, Tyuleniy virus, Uganda S virus, Usutu virus, Wesselsbron virus, West Nile virus, Yaounde virus, Yellow fever virus, Yokose virus, and Zika virus.

4. The method of claim 2 wherein the virus comprises the Coronavirus, and wherein at least one of the following applies:

(a) the Coronavirus comprises at least one of an Alphacoronavirus, a Betacoronavirus, a Gammacoronavirus, and a Deltacoronavirus, (b) the Coronavirus comprises at least one of MERS-CoV, SARS-CoV, and SARS-CoV-2, (c) the at least one surface viral protein or the at least one virus protein comprises NSP6 or a S glycoprotein.

5. The method of claim 1, wherein each occurrence of $R^{1a}$, $R^{1b}$, $R^{1c}$, and $R^{1d}$ is independently selected from the group consisting of hydrogen, $C_1$-$C_6$ alkyl, $C_1$-$C_6$ fluoroalkyl, $C_1$-$C_6$ heteroalkyl, F, Cl, Br, I, —CN, —$NO_2$, and —$OR^5$.

6. The method of claim 1, wherein each occurrence of $R^{2a}$, $R^{2b}$, $R^{2c}$, and $R^{2d}$ is independently selected from the group consisting of hydrogen, $C_1$-$C_6$ alkyl, $C_1$-$C_6$ fluoroalkyl, $C_1$-$C_6$ heteroalkyl, F, Cl, Br, I, —CN, —$NO_2$, and —$OR^5$.

7. The method of claim 1, wherein $R^3$ is CN, F, Cl, Br, I, —$CF_3$, —$CHF_2$, —$OCF_3$, —$OCHF_2$, —C(O)OH, or —C(O)OMe.

8. The method of claim 1, wherein $R^4$ is CN, F, Cl, Br, I, —$CF_3$, —$CHF_2$, —$OCF_3$, —$OCHF_2$, —C(O)OH, or —C(O)OMe.

9. The method of claim 1, wherein the compound is selected from the group consisting of:

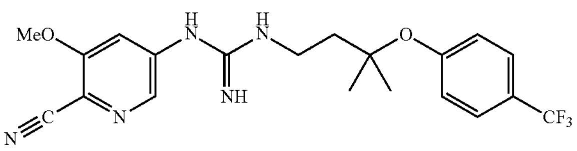 [SMILES: COc1cc(NC(=N)NCCC(C)(C)Oc2ccc(C(F)(F)F)cc2)cnc1C#N]

1-(6-cyano-5-methoxypyridin-3-yl)-3-(3-methyl-3-(4-(trifluoromethyl)phenoxy)butyl)guanidine;

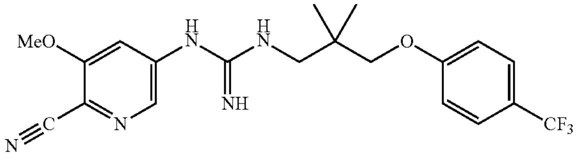 [SMILES: COc1cc(NC(=N)NCC(C)(C)COc2ccc(C(F)(F)F)cc2)cnc1C#N]

1-(6-cyano-5-methoxypyridin-3-yl)-3-(2,2-dimethyl-3-(4-(trifluoromethyl)phenoxy)propyl)guanidine;

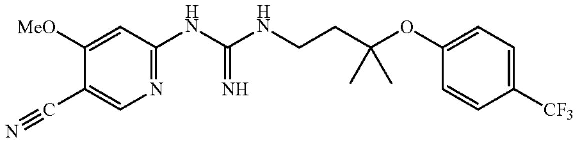 [SMILES: COc1cc(NC(=N)NCCC(C)(C)Oc2ccc(C(F)(F)F)cc2)ncc1C#N]

1-(5-cyano-4-methoxypyridin-2-yl)-3-(3-methyl-3-(4-(trifluoromethyl)phenoxy)butyl)guanidine;

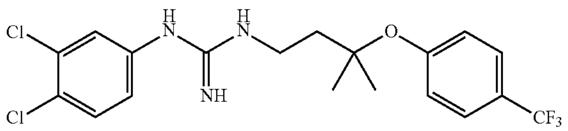 [SMILES: CC(C)(CCNC(=N)Nc1ccc(Cl)c(Cl)c1)Oc1ccc(C(F)(F)F)cc1]

1-(3,4-dichlorophenyl)-3-(3-methyl-3-(4-(trifluoromethyl)phenoxy)butyl)guanidine;

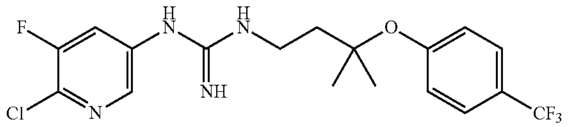 [SMILES: CC(C)(CCNC(=N)Nc1cnc(Cl)c(F)c1)Oc1ccc(C(F)(F)F)cc1]

1-(6-chloro-5-fluoropyridin-3-yl)-3-(3-methyl-3-(4-(trifluoromethyl)phenoxy)butyl)guanidine;

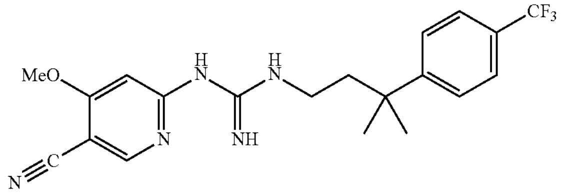 [SMILES: COc1cc(NC(=N)NCCC(C)(C)c2ccc(C(F)(F)F)cc2)ncc1C#N]

1-(5-cyano-4-methoxypyridin-2-yl)-3-(3-methyl-3-(4-(trifluoromethyl)phenyl)butyl)guanidine;

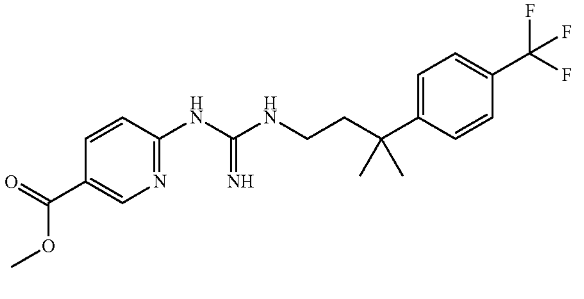 [SMILES: COC(=O)c1ccc(NC(=N)NCCC(C)(C)c2ccc(C(F)(F)F)cc2)nc1]

methyl 6-(3-(3-methyl-3-(4-(trifluoromethyl)phenyl)butyl)guanidino)nicotinate;

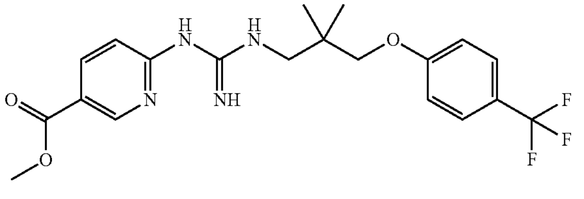 [SMILES: COC(=O)c1ccc(NC(=N)NCC(C)(C)COc2ccc(C(F)(F)F)cc2)nc1]

methyl 6-(3-(2,2-dimethyl-3-(4-(trifluoromethyl)phenoxy)propyl)guanidino)nicotinate;

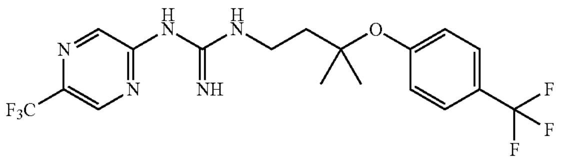 [SMILES: CC(C)(CCNC(=N)Nc1cnc(C(F)(F)F)cn1)Oc1ccc(C(F)(F)F)cc1]

1-(3-methyl-3-(4-(trifluoromethyl)phenoxy)butyl)-3-(2-(trifluoromethyl)pyrimidin-5-yl)guanidine;

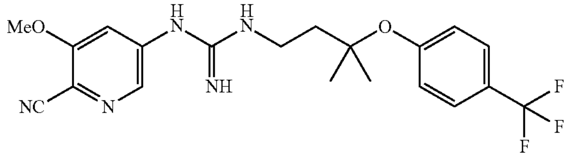 [SMILES: COc1cc(NC(=N)NCCC(C)(C)Oc2ccc(C(F)(F)F)cc2)cnc1C#N]

1-(6-cyano-5-methoxypyridin-3-yl)-3-(3-methyl-3-(4-(trifluoromethyl)phenoxy)butyl)guanidine;

or a salt, solvate, tautomer, or N-oxide thereof.

10. The method of claim 1, wherein at least one of the following applies:

(a) the compound is administered to the subject as a pharmaceutical composition further comprising a pharmaceutically acceptable carrier, (b) the subject is further administered at least one additional antiviral agent or at least one agent that treats, ameliorates, or prevents one or more virus infection symptoms or co-morbidities, (c) the compound is administered to the subject by a route comprising oral, nasal, rectal, intravaginal, parenteral, buccal, sublingual, or topical, (d) the subject is a mammal, (e) the subject is a human.

11. A compound of formula (I):

(I)

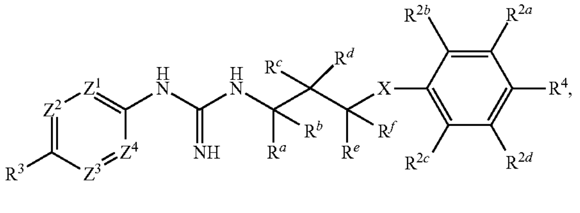

wherein:

one of the following applies:

| | | | |
|---|---|---|---|
| (a) $Z^1$ is $CR^{1a}$; | $Z^2$ is N; | $Z^3$ is $CR^{1c}$ or N; | $Z^4$ is $CR^{1d}$; |
| (b) $Z^1$ is N; | $Z^2$ is $CR^{1b}$; | $Z^3$ is $CR^{1c}$; | $Z^4$ is $CR^{1d}$ or N; |
| (c) $Z^1$ is $CR^{1a}$; | $Z^2$ is N; | $Z^3$ is $CR^{1c}$; | $Z^4$ is N; |
| (d) $Z^1$ is N; | $Z^2$ is $CR^{1b}$; | $Z^3$ is N; | $Z^4$ is $CR^{1d}$; |

X is selected from the group consisting of bond and O;

each occurrence of $R^{1a}$, $R^{1b}$, $R^{1c}$, and $R^{1d}$ is independently selected from the group consisting of hydrogen, $C_1$-$C_6$ alkyl, $C_1$-$C_6$ fluoroalkyl, $C_1$-$C_6$ heteroalkyl, F, Cl, Br, I, —CN, —$NO_2$, —$OR^5$, —$SR^5$, —S(=O)$R^5$, —$S(=O)_2R^5$, —$NHS(=O)_2R^5$, —C(=O)$R^5$, —OC(=O)$R^5$, —$CO_2R^5$, —$OCO_2R^5$, —$CH(R^5)_2$, —$N(R^5)_2$, —C(=O)$N(R^5)_2$, —OC(=O)$N(R^5)_2$, —NHC(=O)NH($R^5$), —NHC(=O)$R^5$, —NHC(=O)$OR_5$, —C(OH)$(R^5)_2$, and —$C(NH_2)(R^5)_2$;

each occurrence of $R^{2a}$, $R^{2b}$, $R^{2c}$, and $R^{2d}$ is independently selected from the group consisting of hydrogen, $C_1$-$C_6$ alkyl, $C_1$-$C_6$ fluoroalkyl, $C_1$-$C_6$ heteroalkyl, F, Cl, Br, I, —CN, —$NO_2$, —$OR^5$, —$SR^5$, —S(=O)$R^5$, —$S(=O)_2R^5$, —$NHS(=O)_2R^5$, —C(=O)$R^5$, —OC(=O)$R^5$, —$CO_2R^5$, —$OCO_2R^5$, —$CH(R^5)_2$, —$N(R^5)_2$, —C(=O)$N(R^5)_2$, —OC(=O)$N(R^5)_2$, —NHC(=O)NH($R^5$), —NHC(=O)$R^5$, —NHC(=O)$OR^5$, —C(OH)$(R^5)_2$, and —$C(NH_2)(R^5)_2$;

$R^3$ is selected from the group consisting of CN, F, Cl, Br, I, $C_1$-$C_6$ haloalkyl, $C_1$-$C_6$ haloalkoxy, and —C(O)$OR^6$;

$R^4$ is selected from the group consisting of CN, F, Cl, Br, I, $C_1$-$C_6$ haloalkyl, $C_1$-$C_6$ haloalkoxy, and —C(O)$OR^7$;

each occurrence of $R^5$ is independently selected from the group consisting of H, $C_1$-$C_6$ alkyl, $C_1$-$C_6$ heteroalkyl, aryl, and —$C_1$-$C_3$ alkyl-($C_3$-$C_6$ cycloalkyl), wherein the alkyl, heteroalkyl, aryl, or cycloalkyl group is optionally substituted;

$R^6$ is selected from the group consisting of H, $C_1$-$C_6$ alkyl, $C_1$-$C_6$ heteroalkyl, and $C_3$-$C_6$ cycloalkyl, wherein the alkyl, heteroalkyl, or cycloalkyl group is optionally substituted;

$R^7$ is selected from the group consisting of H, $C_1$-$C_6$ alkyl, $C_1$-$C_6$ heteroalkyl, and $C_3$-$C_6$ cycloalkyl, wherein the alkyl, heteroalkyl, or cycloalkyl group is optionally substituted; and each occurrence of $R^a$, $R^b$, $R^c$, $R^d$, $R^e$, and $R^f$ is independently selected from the group consisting of H and $CH_3$, with the proviso that, if $Z^3$ is $CR^{1c}$ and $Z^4$ is $CR^{1d}$, then at least one of $R^a$, $R^b$, $R^c$, $R^d$, $R^e$, and $R^f$ is $CH_3$, or a salt, solvate, enantiomer, diastereoisomer, tautomer, or N-oxide thereof.

12. The compound of claim 11, wherein each occurrence of $R^{1a}$, $R^{1b}$, $R^{1c}$, and $R^{1d}$ is independently selected from the group consisting of hydrogen, $C_1$-$C_6$ alkyl, $C_1$-$C_6$ fluoroalkyl, $C_1$-$C_6$ heteroalkyl, F, Cl, Br, I, —CN, —$NO_2$, and —$OR^5$.

13. The compound of claim 11, wherein each occurrence of $R^{2a}$, $R^{2b}$, $R^{2c}$, and $R^{2d}$ is independently selected from the group consisting of hydrogen, $C_1$-$C_6$ alkyl, $C_1$-$C_6$ fluoroalkyl, $C_1$-$C_6$ heteroalkyl, F, Cl, Br, I, —CN, —$NO_2$, and —$OR^5$.

14. The compound of claim 11, wherein $R^3$ is CN, F, Cl, Br, I, —$CF_3$, —$CHF_2$, —$OCF_3$, —$OCHF_2$, —C(O)OH, or —C(O)OMe.

15. The compound of claim 11, wherein $R^4$ is CN, F, Cl, Br, I, —$CF_3$, —$CHF_2$, —$OCF_3$, —$OCHF_2$, —C(O)OH, or —C(O)OMe.

16. A compound selected from the group consisting of:

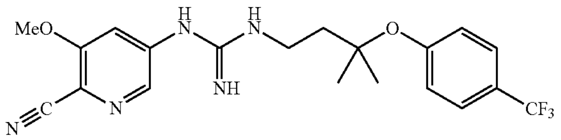 [SMILES: COc1cc(NC(=N)NCCC(C)(C)Oc2ccc(C(F)(F)F)cc2)cnc1C#N]

1-(6-cyano-5-methoxypyridin-3-yl)-3-(3-methyl-3-(4-(trifluoromethyl)phenoxy)butyl)guanidine;

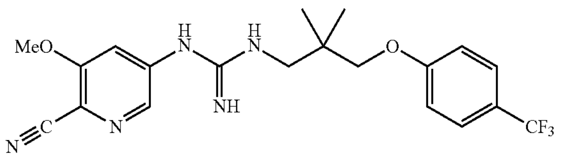 [SMILES: COc1cc(NC(=N)NCC(C)(C)COc2ccc(C(F)(F)F)cc2)cnc1C#N]

1-(6-cyano-5-methoxypyridin-3-yl)-3-(2,2-dimethyl-3-(4-(trifluoromethyl)phenoxy)propyl)guanidine;

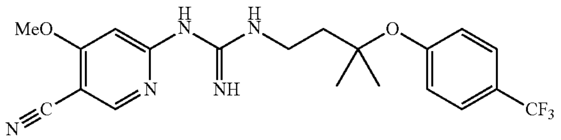 [SMILES: COc1cc(NC(=N)NCCC(C)(C)Oc2ccc(C(F)(F)F)cc2)ncc1C#N]

1-(5-cyano-4-methoxypyridin-2-yl)-3-(3-methyl-3-(4-(trifluoromethyl)phenoxy)butyl)guanidine;

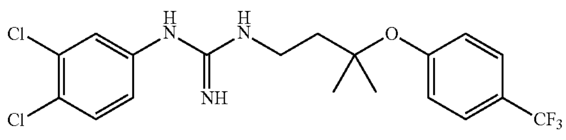 [SMILES: CC(C)(CCNC(=N)Nc1ccc(Cl)c(Cl)c1)Oc1ccc(C(F)(F)F)cc1]

1-(3,4-dichlorophenyl)-3-(3-methyl-3-(4-(trifluoromethyl)phenoxy)butyl)guanidine;

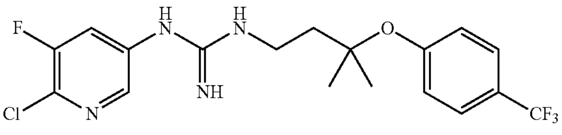

1-(6-chloro-5-fluoropyridin-3-yl)-3-(3-methyl-3-(4-(trifluoromethyl)phenoxy)butyl)guanidine;

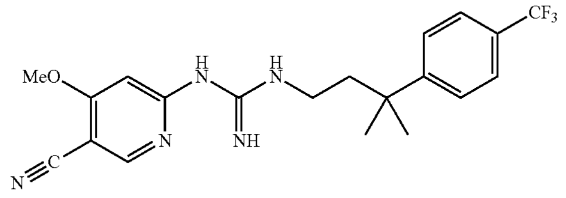 [SMILES: COc1cc(NC(=N)NCCC(C)(C)c2ccc(C(F)(F)F)cc2)ncc1C#N]

1-(5-cyano-4-methoxypyridin-2-yl)-3-(3-methyl-3-(4-(trifluoromethyl)phenyl)butyl)guanidine;

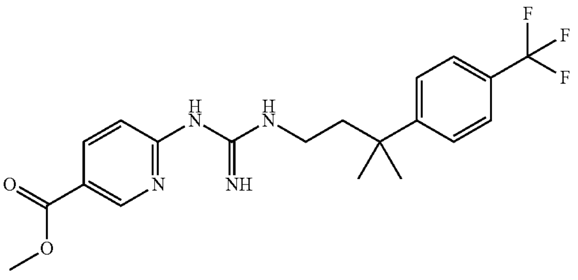 [SMILES: COC(=O)c1ccc(NC(=N)NCCC(C)(C)c2ccc(C(F)(F)F)cc2)nc1]

methyl 6-(3-(3-methyl-3-(4-(trifluoromethyl)phenyl)butyl)guanidino) nicotinate;

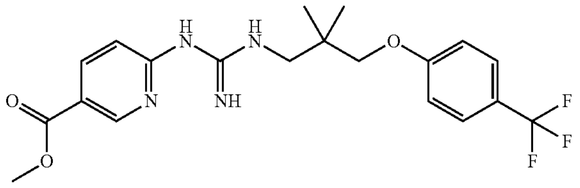 [SMILES: COC(=O)c1ccc(NC(=N)NCC(C)(C)COc2ccc(C(F)(F)F)cc2)nc1]

methyl 6-(3-(2,2-dimethyl-3-(4-(trifluoromethyl)phenoxy)propyl)guanidino)nicotinate;

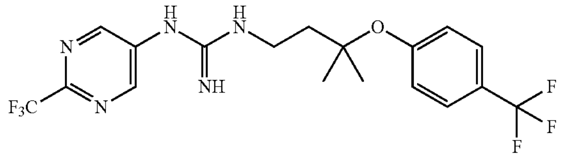 [SMILES: CC(C)(CCNC(=N)Nc1cnc(C(F)(F)F)nc1)Oc1ccc(C(F)(F)F)cc1]

1-(3-methyl-3-(4-(trifluoromethyl)phenoxy)butyl)-3-(2-(trifluoromethyl)pyrimidin-5-yl)guanidine;

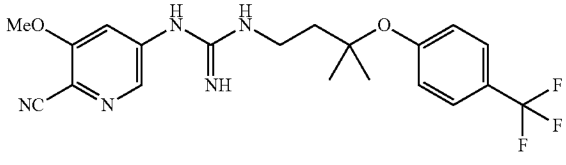 [SMILES: COc1cc(NC(=N)NCCC(C)(C)Oc2ccc(C(F)(F)F)cc2)cnc1C#N]

1-(6-cyano-5-methoxypyridin-3-yl)-3-(3-methyl-3-(4-(trifluoromethyl)phenoxy)butyl)guanidine;

or a salt, solvate, tautomer, or N-oxide thereof.

17. A pharmaceutical composition comprising at least one pharmaceutically acceptable carrier and at least one compound of claim 11.

18. The pharmaceutical composition of claim 17, further comprising at least one additional antiviral agent or at least one agent that treats, ameliorates, or prevents one or more virus infection symptoms or co-morbidities.

19. The pharmaceutical composition of claim 17, which is formulated for administration by at least one of oral, nasal, rectal, intravaginal, parenteral, buccal, sublingual, and topical routes.

* * * * *